(12) United States Patent
Carroll et al.

(10) Patent No.: US 8,062,687 B2
(45) Date of Patent: Nov. 22, 2011

(54) HIGH PRESSURE PROCESSING OF BIOACTIVE COMPOSITIONS

(75) Inventors: Timothy Joseph Carroll, Palmerston North (NZ); Hasmukh Ambalal Patel, Palmerston North (NZ); Miguel Alejandro Gonzalez-Martin, Hamburg (DE); James William Dekker, Palmerston North (NZ); Michael Anthony Collett, Palmerston North (NZ); Marc William Lubbers, Melbourne (AU)

(73) Assignee: Fonterra Co-Operative Group Limited, Auckland (NZ)

( * ) Notice: Subject to any disclaimer, the term of this patent is extended or adjusted under 35 U.S.C. 154(b) by 904 days.

(21) Appl. No.: 11/908,106

(22) PCT Filed: Mar. 8, 2006

(86) PCT No.: PCT/NZ2006/000039
§ 371 (c)(1),
(2), (4) Date: Feb. 6, 2008

(87) PCT Pub. No.: WO2006/096074
PCT Pub. Date: Sep. 14, 2006

(65) Prior Publication Data
US 2008/0317823 A1  Dec. 25, 2008

(30) Foreign Application Priority Data

Mar. 8, 2005 (NZ) ......................................... 538671
Dec. 23, 2005 (NZ) ......................................... 544408

(51) Int. Cl.
*A23C 7/00* (2006.01)
*A23C 23/00* (2006.01)
*A23J 1/00* (2006.01)

(52) U.S. Cl. .......... 426/580; 426/61; 426/601; 426/656; 426/657; 426/658

(58) Field of Classification Search ................ 426/61, 426/580, 601, 656, 657, 658
See application file for complete search history.

(56) References Cited

U.S. PATENT DOCUMENTS

2002/0182107 A1   12/2002   Laugharn et al.
2003/0103863 A1   6/2003    Grislain et al.

FOREIGN PATENT DOCUMENTS

| DE | 19801031 A1 | 7/1999 |
| JP | 4-218360 | 8/1992 |
| JP | 4218360 A | 8/1992 |
| JP | 2003009760 A | 1/2003 |
| WO | WO 00/48641 A1 | 8/2000 |
| WO | WO 2004/032655 A1 | 4/2004 |

OTHER PUBLICATIONS

Masschalck, B. et al. "High pressure increases bactericidal activity and spectrum of lactoferrin, lactoferricin and nisin" International Journal of Food Microbiology, 2001, 64(3): 325-329.
Oshima, T. et al. "High-pressure processing of fish and fish products" Trends in Food Science & Technology, Nov. 1993, 4(11): 370-375.
Puig et al. "Microbiological and biochemical stabilization of wines using high-pressure technique" Bulletin de L'O.I.V., 2003, 76(869-870): 596-617.
Vardag, T. and Koerner, P. "High pressure: a real alternative in food processing" Food Marketing & Technology, Feb. 1995, 9(1): 42-47.
International Search Report dated Jun. 9, 2006, for International Application No. PCT/NZ2006/000039, in 5 pages.
International Preliminary Report on Patentability, dated Jun. 15, 2007, received for International Application No. PCT/NZ2006/000039, in 8 pages.
File Wrapper for U.S. Appl. No. 11/908,107, titled "High Pressure Processing of Metal Ion Lactoferrin", listing as inventor Palmano et al.
International Preliminary Report on Patentability, dated Jun. 15, 2007, received in International Application No. PCT/NZ2006/000038, 6 pages.
International Search Report dated Jun. 9, 2006, received in International Application No. PCT/NZ2006/000038, 6 pages.

*Primary Examiner* — Leslie Wong
(74) *Attorney, Agent, or Firm* — Knobbe Martens Olson & Bear LLP

(57) ABSTRACT

The present invention relates to a method of pressure treating a bioactive composition comprising at least one bioactive component to prevent the growth of at least one unwanted microorganism while retaining a desired level activity of the at least one bioactive component. The bioactive component is selected from one or more proteins protein hydrolysates, one or more lipids or lipid hydrolysates, one or more carbohydrates, one or more probiotic factors, or mixtures thereof. The pressure treatment is at a predetermined pressure from about 350 to 1000 MPa.

41 Claims, 10 Drawing Sheets

HIGH PRESSURE PROCESSING OF BIOACTIVE COMPOSITIONS

REFERENCE TO RELATED APPLICATIONS

The present application is the U.S. National Phase under 35 U.S.C. §371 of International PCT application number PCT/NZ2006/000039, filed Mar. 8, 2006, which claims priority to New Zealand Application No. 538671, filed Mar. 8, 2005, and New Zealand Application No. 544408, filed Dec. 23, 2005, each of which is incorporated herein by reference in its entirety.

FIELD OF INVENTION

The present invention relates to the high pressure processing of bioactive compositions and in particular to a method of pressure treating a bioactive composition to prevent the growth of at least one unwanted microorganism while retaining a desired level of activity of at least one bioactive component.

BACKGROUND

The delivery of bioactive components (proteins, lipids or hydrolysates thereof, and probiotic microorganisms, for example) in food or other ingestible products is constrained by the need to provide a safe product with a useful shelf life while retaining bioactivity. Products with a useful shelf life are said to have a good keeping quality and are less prone to spoilage.

Delivery of bioactive components is desirable at least because such components are physiologically active when ingested and can have positive health benefits, including but not limited to bone health, immune benefits, anti-inflammatory activity, heart health and efficacy in cancer treatment.

Traditional means of ensuring a useful keeping quality have a negative impact on the bioactivity of food products and the like. In particular, thermal processing is not generally suitable for the production of commercially sterile bioactive products. For example, an analysis of immunoglobulin proteins in commercial dairy products revealed that although between 60% and 75% of the immunoglobulins are retained through pasteurisation, levels in UHT or canned (evaporated) milk are negligible (Li-Chan et al, 1995). Commercial sterility in acid foods may be achieved by employing a lower-temperature heating than that used in canning, but the sensitivity of immunoglobulins to denaturing under heating is exacerbated by acidification (Dominguez et al, 2001).

A probiotic microorganism is one that when administered in an adequate amount confers a health benefit on the host. While the live probiotic microorganism exhibits a bioactive effect, an inactivated probiotic microorganism may provide the bioactivity in a stable, less technically restricted format for use and distribution. In applications where it is undesirable to have live microorganisms because of their unwanted activities (such as enzyme or acid secretion, for example), inactivated microorganisms may be advantageous in still providing the bioactivity, without the unwanted activity resulting from their viability. International PCT application WO 20041032655 reports use of high pressure treatment to reduce microbial spoilage in foods and/or to render the food safe for consumption, while retaining viable desired cultures.

There are many processes in the manufacture of bioactive products, ingredients and foods that may result in a partial or complete loss of bioactivity. In the case of dairy-based ingredients and foods, processes that involve heating steps that may affect bioactivity include thermal pasteurisation, homogenisation, thermalisation, evaporation and drying. In the case of food processing, examples of heating steps that may affect bioactivity include heat treatments preceding fermentation, UHT-treatments, retorting, hot filling and hot packing. A bioactive component will typically be subjected to one or more of these heating steps during the manufacture of a food. This is particularly true of dairy-based products where processing always includes an initial pasteurisation step and typically includes further heating steps prior to packaging and sale. Korhonen et al (1998) report that heating to temperatures in the range 60° C. to 90° C. denatures proteins therefore reducing the activity of bioactive proteins.

Drying of products produced using pasteurised milk may be used to improve keeping quality with losses of up to 40% of immunoglobulins (Li-Chan, 1995), but commercial applications are then limited to direct consumption (for example, tablets) or fresh products (for example, yogurt) where the dried bioactive ingredient is not subsequently heated again. Losses due to drying and heating may be compensated for by supplementing intermediate or final products with the bioactive component of interest but this can increase the cost to the end consumer.

Pressure treatment with pressures above about 350 MPa has been reported to achieve commercially-useful improvements in keeping quality for meat, vegetable and fruit-based products (such as cooked ham, avocado products and juices respectively). However, Huppertz et al (2002) report that high pressure denatures whey proteins in milk. Additionally, Korhonen et al (1998) report that pressure treatments at pressures of about 500 MPa and above irreversibly denature proteins in most cases. Felipe et al (1997) report that appreciable levels of immunoglobulin denaturation occur in goat's milk at pressures of 500 MPa.

Masuda et al (2000) report that pressures of 400 MPa and above may not be used to improve the keeping quality of bovine colostrum because such pressures denature the immunoglobulin protein.

Tonello et al (1992) report that pressures of 200 MPa applied for 2 hours may be used to retain at least 85% of the immunoglobulin activity, although the microbial load of colostrum is reduced by less than 2-log cycles. The same process at 63° C. can reduce the microbial load below limits of detection (more than 7-log cycles), but at least 50% of the immunoglobulin activity is lost.

The need exists for a process that can provide a commercially useful keeping quality for a bioactive product such as a food or other ingestible product while retaining the bioactivity of at least one bioactive component.

Therefore it is an object of this invention to provide an improved or alternative method of preventing the growth of unwanted microorganisms while retaining at least a desired level of activity of at least one bioactive component or to at least provide the public with a useful choice.

SUMMARY OF INVENTION

The present invention relates to methods for maintaining or increasing the keeping quality of a bioactive composition while retaining at least a desired level of activity of at least one bioactive component that is present in the composition.

Accordingly, in one aspect the present invention relates to a method of treating a bioactive composition to maintain or increase its keeping quality comprising:

(a) selecting a bioactive composition comprising at least one bioactive component selected from one or more proteins, one or more lipids, one or more protein hydrolysates, one or more lipid hydrolysates, one or more carbohydrates, or one or more probiotic factors, or a mixture thereof, the at least one bioactive component being able to retain a desired level of activity after a pressure treatment at a predetermined pressure of from about 350 to 1000 MPa and pH of from about 3.0 to 8.0; and (b) subjecting the composition to a pressure treatment at the predetermined pressure and pH to prevent the growth of unwanted organisms that may be present in the composition while retaining at least a desired level of activity of the at least one bioactive component.

In another aspect the present invention relates to a method of treating a bioactive composition to maintain or increase its keeping quality comprising:

(a) selecting a bioactive composition comprising at least one bioactive component selected from one or more proteins, one or more lipids, one or more protein hydrolysates, one or more lipid hydrolysates, one or more carbohydrates, or one or more probiotic factors, or a mixture thereof, the at least one bioactive component being able to retain a desired level of activity after a pressure treatment at a predetermined pressure of from about 350 to 1000 MPa, pH of from about 3.0 to 8.0 and hold time of from about 0 to 5 minutes; and (b) subjecting the composition to a pressure treatment at the predetermined pressure, pH and hold time to prevent the growth of unwanted organisms that may be present in the composition while retaining at least a desired level of activity of the at least one bioactive component.

In another aspect the present invention relates to a method of treating a probiotic composition comprising:

(a) selecting a composition comprising one or more strains of probiotic microorganism having one or more probiotic factors, the probiotic factors being able to retain at least a desired level of activity after a pressure treatment at a predetermined pressure of from about 350 to 1000 MPa; and (b) subjecting the composition to a pressure treatment at the predetermined pressure to prevent the growth of the one or more strains of probiotic microorganism while retaining at least a desired level of activity of one or more probiotic factors.

In another aspect the present invention relates to a method of treating a probiotic composition comprising:

(a) selecting a composition comprising one or more strains of probiotic microorganism selected from one or more *Lactobacillus acidophilus* strains, one or more *Lactobacillus rhamnosus* strains, or one or more *Bifidiobacterium animalis* subsp. *lactis* strains, or a mixture thereof, the one or more strains of probiotic microorganism having one or more probiotic factors, the probiotic factors being able to retain at least a desired level of activity after a pressure treatment at a predetermined pressure of from about 350 to 1000 MPa; and (b) subjecting the composition to a pressure treatment at the predetermined pressure to prevent the growth of the one or more strains of probiotic microorganism while retaining at least a desired level of activity of one or more probiotic factors.

The following embodiments may relate to any of the aspects described above or below.

The composition may be a liquid including a suspension of a solid in a liquid. The composition may be a product or ingredient. Preferably, treating the composition to maintain or improve keeping quality comprises treating to reduce, delay, prevent or eliminate the growth of at least one unwanted microorganism, preferably all unwanted microorganisms.

In one embodiment the post-treatment aerobic plate count (APC) is less than or equal to about 100,000, 75,000, 50,000, 25,000, 10,000, 5,000, 1,000, 100, or 10 colony forming units per millilitre (cfu/ml), preferably less than or equal to about 50,000 cfu/ml.

In one embodiment the one or more proteins may be recombinant, synthetic or naturally occurring proteins, or a mixture thereof.

In one embodiment the at least one bioactive component is selected from lactoferrin, lysozyme, one or more IgA, one or more IgD, one or more IgE, one or more IgG, one or more IgM, one or more milk derived growth factors, TGF β1, TGF β2, or one or more probiotic factors, or a mixture thereof.

In another embodiment the at least one bioactive component comprises one or more probiotic factors.

In yet another embodiment the bioactive composition comprises a dairy protein composition. Preferably in this embodiment the at least one bioactive component is selected from lactoferrin, lysozyme, one or more IgA, one or more IgD, one or more IgE, one or more IgG, one or more IgM, one or more milk derived growth factors, TGF β1, or TGF β2, or a mixture thereof.

In still another embodiment the bioactive composition is selected from colostrum MPC, colostrum MPI, colostrum WPC, colostrum WPI, MPC, MPI, WPC, WPI, hyperimmune MPC, hyperimmune MPI, hyperimmune WPC, or hyperimmune WPI, or a mixture thereof. Preferably in this embodiment the at least one bioactive component is selected from lactoferrin, lysozyme, one or more IgA, one or more IgD, one or more IgE, one or more IgG, one or more IgM, TGF β1, or TGF β2, or a mixture thereof.

In another embodiment the bioactive component is selected from lactoferrin, lysozyme, one or more immunoglobulins (including one or more IgA, IgD, IgE, IgG or IgM, or a mixture thereof, or a plurality of one or more of IgA, IgD, IgE, IgG or IgM specific for different epitopes), glycomacropeptide, one or more growth factors (including one or more milk derived growth factors), TGF β1, TGF β2, one or more probiotic factors, one or more non-polar lipids, or one or more polar lipids (such as one or more phospholipids, sphingolipids, gangliosides, or ceramides, or a mixture thereof), or a mixture thereof. In a preferred embodiment, the bioactive component is selected from lactoferrin, lysozyme, one or more IgA, one or more IgD, one or more IgE, one or more IgG, one or more IgM, one or more growth factors, TGF β1, TGF β2, one or more probiotic factors, one or more non-polar lipids, one or more phospholipids, one or more sphingolipids, one or more gangliosides, or one or more ceramides, or a mixture thereof. In an alternative preferred embodiment, the bioactive component is selected from lactoferrin, one or more IgA, one or more IgG, one or more IgM, TGF β1, TGF β2, or one or more probiotic factors, or a mixture thereof.

In one embodiment the composition comprises, consists essentially of or consists of a bioactive component selected from lactoferrin, lysozyme, one or more immunoglobulins (including one or more IgA, IgD, IgE, IgG or IgM, or a mixture thereof, or a plurality of one or more of IgA, IgD, IgE, IgG or IgM specific for different epitopes), glycomacropeptide, one or more growth factors (including milk derived growth factors, including TGF β1 and TGF β2), or one or more probiotic factors, or a mixture thereof.

In another embodiment the composition comprises, consists essentially of or consists of a bioactive component selected from one or more non-polar lipids, one or more polar lipids such as phospholipids, sphingolipids, gangliosides, or ceramides, or a mixture thereof.

In one embodiment the composition comprises, consists essentially of or consists of at least about 0.01, 0.05, 0.1, 0.5, 1, 5, 10, 15, 20, 25, 30, 35, 40, 45, 50, 55, 60, 65, 70, 75, 80, 85, 90, 95, 99, 99.5 or 100% by weight of a bioactive component selected from lactoferrin, lysozyme, one or more immunoglobulins (including one or more IgA, IgD, IgE, IgG or IgM, or a mixture thereof, or a plurality of one or more of IgA, IgD, IgE, IgG or IgM specific for different epitopes), glycomacropeptide, growth factors (including milk derived growth factors, including TGF β1 and TGF β2), or one or more probiotic factors, or a mixture thereof.

In one embodiment the composition is enriched with a composition consisting essentially of or consisting of a bioactive component selected from lactoferrin, lysozyme, one or more immunoglobulins (including one or more IgA, IgD, IgE, IgG or IgM, or a mixture thereof, or a plurality of one or more of IgA, IgD, IgE, IgG or IgM specific for different epitopes), glycomacropeptide, growth factors (including milk derived growth factors, including TGF β1 and TGF β2), a composition comprising at least about 1% w/w immunoglobulin, a product made by inoculating an animal to increase antibody levels, immune milk, or one or more probiotic factors, or a mixture thereof. That is, a composition consisting essentially of or consisting of a bioactive component such as lactoferrin, lysozyme, one or more immunoglobulins (including one or more IgA, IgD, IgE, IgG or IgM, or a mixture thereof, or a plurality of one or more of IgA, IgD, IgE, IgG or IgM specific for different epitopes), glycomacropeptide, growth factors (including milk derived growth factors, including TGF β1 and TGF β2), a composition comprising at least about 1% W/W immunoglobulin, a product made by inoculating an animal to increase antibody levels (hyperimmune milk or hyperimmune colostrum), immune milk, or one or more probiotic factors, or a mixture thereof, is added to the composition to increase the concentration of the bioactive component.

In one embodiment the probiotic factor is selected from one or more bacterial DNA motifs, one or more bacterial surface proteins, one or more bacterial small organic acids, or one or more bacterial cell wall components, or a mixture thereof.

In one embodiment the unwanted organism is selected from one or more bacteria (including probiotic bacteria), one or more fungi, one or more molds, or one or more yeasts and one or more algae, or a mixture thereof. In one embodiment the unwanted organism is a spoilage organism selected from one or more bacteria, one or more fungi, one or more molds, one or more yeasts or one or more algae, or a mixture thereof. In one embodiment the unwanted organism is a pathogen selected from one or more bacteria, one or more fungi, one or more molds, one or more yeasts or one or more algae, or a mixture thereof. In an alternative embodiment the unwanted organism comprises a probiotic organism and optionally an additional unwanted organism.

In one embodiment the unwanted organism or the probiotic microorganism is selected from the group consisting of *Lactobacillus, Streptococcus, Lactococcus, Leuconostoc, Pediococcus, Bifidobacterium, Propionibacterium, Enterococcus* or *Bacillus*, or a mixture thereof. In another embodiment the microorganism is selected from the group consisting of *Lactobacillus acidophilus, Lactobacillus delbrueckil* subsp. *bulgaricus, Lactobacillus casei, Lactobacillus crispatus, Lactobacillus johnsonii, Lactobacillus plantarum, Lactobacillus reuteri, Lactobacillus rhamnosus, Lactobacillus salivarius, Bifidiobacterium bifidum, Bifidiobacterium breve, Bifidobacterium infantis, Bifidiobacterium animalis* subsp. *lactis, Bifidobacterium longum,* or *Streptococcus thermophilus,* or a mixture thereof.

In another embodiment the unwanted organism or the probiotic microorganism is selected from the group consisting of *Lactobacillus rhamnosus* HN001 (AGAL NM 97/09514), *Bifidiobacterium animalis* subsp. *lactis* HN019 (AGAL NM 97/09513), *Lactobacillus acidophilus* HN017 (AGAL NM 97/09515), *Lactobacillus rhamnosus* HN067 (AGAL NM 97/01925) (all of which are described in U.S. Pat. No. 6,379,663), *Lactobacillus johnsonii* NCC533 (La1) (CNCM I-1225), *Lactobacillus rhamnosus* GG (ATCC 53103), *Lactobacillus casei* Shirota (FERM-P4751), *Lactobacillus acidophilus* NCFM (ATCC 700396), *Lactobacillus plantarum* 299v (DSMZ 9843), *Lactobacillus casei* DN114001 (CNCM I-1518), *Lactobacillus salivarius* UCC4331 (NCIMB 40829), *Bifidiobacterium animalis* subsp. *lactis* BB12 (ATCC 27536 and DSMZ 10140), or *Bifidobacterium infantis* 35624 (NCIMB 41003), or a mixture thereof. Preferred unwanted organisms or probiotic microorganisms include *Lactobacillus rhanmosus* HN001, *Bifidiobacterium animalis* subsp. *lactis* HN019, *Lactobacillus acidophilus* HN017, or *Lactobacillus rhamnosus* HN067, or a mixture thereof.

In one embodiment the probiotic microorganism is an inactivated probiotic microorganism. An inactivated probiotic microorganism may be non-viable, non-viable but still metabolically active, or dead.

In one embodiment the composition comprises one or more unwanted microorganisms, such as one or more bacteria (including one or more probiotic bacteria), one or more fungi, one or more molds, one or more yeasts, or one or more algae, or a mixture thereof. It should be understood that in one embodiment the methods useful herein are preferably intended to prevent the growth of at least one unwanted microorganism. However, often the method may be carried out prophylactically and there may not actually be any unwanted organisms present. In such cases, the method is carried out to maintain or improve keeping quality or to comply with food safety requirements, current good manufacturing practice or regulatory requirements. Regardless of the presence or absence of an unwanted microorganism, a pressure treatment method useful herein retains at least a desired level of activity of at least one bioactive component and is useful to maintain or increase keeping quality.

Therefore, the method preferably prevents the growth of at least one unwanted microorganism while retaining at least a desired level of activity of at least one bioactive component.

In one embodiment the composition is milk, including sheep, goat, pig, mouse, water buffalo, camel, yak, horse, donkey, llama, bovine or human milk, or a mixture thereof. Preferably the milk is bovine milk.

In another embodiment the composition comprises dairy protein or is a dairy ingredient. Preferably the dairy protein composition or the dairy ingredient is recombined or fresh whole milk, recombined or fresh skim milk, reconstituted whole or skim milk powder, skim milk concentrate, skim milk isolate, whole or skim milk powder, skim milk retentate, concentrated milk, buttermilk, ultrafiltered milk retentate, milk protein concentrate (MPC), milk protein isolate (MPI), calcium depleted milk protein concentrate, calcium depleted milk protein isolate, low fat milk, low fat milk protein concentrate, low fat milk protein isolate, colostrum, a colostrum fraction, colostrum protein concentrate (CPC), colostrum milk protein concentrate, colostrum milk protein isolate, colostrum whey, colostrum whey protein concentrate, colostrum whey protein isolate, an immunoglobulin fraction from colostrum, whey, whey protein concentrate (WPC), whey protein isolate (WPI), sweet whey, lactic acid whey, mineral acid whey, reconstituted whey powder, hyperimmune milk, hyperimmune milk protein concentrate, hyperimmune milk protein isolate, hyperimmune whey, hyperimmune whey protein concentrate, hyperimmune whey protein isolate, hyperimmune colostrum, hyperimmune colostrum milk protein concentrate, hyperimmune colostrum milk protein isolate, hyperimmune colostrum whey, hyperimmune colostrum whey protein concentrate, hyperimmune colostrum whey protein isolate, a composition derived from any milk or colostrum processing stream, a composition derived from the retentate or permeate obtained by ultrafiltration or microfiltration of any milk or colostrum processing stream, or a composition derived from the breakthrough or adsorbed fractions obtained by chromatographic separation of any milk or colostrum processing stream, or a full or partial hydrolysates of any of these compositions, or a mixture thereof.

Preferably the dairy protein composition or dairy ingredient is from a cow, sheep, goat, pig, mouse, water buffalo, camel, yak, horse, donkey, llama or human source, or a mixture thereof.

In another embodiment a probiotic composition is a dairy composition, such as those described above.

In one embodiment the composition is pasteurised, dried, evaporated or filtered (including membrane filtration) before being subjected to the treatment pressure.

In another embodiment, the desired level of activity is at least about 35, 40, 45, 50, 55, 60, 65, 70, 75, 80, 85, 90, 95, 99 or 100% of the activity of an untreated control, and useful ranges may be selected between any of these values (for example, from about 35 to about 100%, from about 50 to about 100%, from about 60 to about 100%, from about 70 to about 100%, from about 80 to about 100%, and from about 90 to about 100%). Preferably the at least one bioactive component is a protein and the retained activity is assessed by ELISA, flow cytometry, HPLC or BiaCore. Preferably the at least one bioactive component is a lipid and the retained activity is assessed by flow cytometry, gas chromatography (GC) or HPLC. Preferably the probiotic activity is assessed by flow cytometry or PBMC cytokine secretion assay. Preferably the desired level of activity is at least about 35% of the activity of an untreated control, at least about 50% of the activity of an untreated control, at least about 60% of the activity of an untreated control, at least about 70% of the activity of an untreated control, at least about 80% of the activity of an untreated control, or at least about 90, 95, 99 or 100% of the activity of an untreated control.

In one embodiment the treatment pressure is selected from at least about 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 750, 800, 850, 900, 950 and 1000 MPa or greater, and useful ranges may be selected between any of these values (for example, from about 350 to about 400 MPa, from about 350 to about 450 MPa, from about 350 to about 500 MPa, from about 350 to about 550 MPa, from about 350 to about 600 MPa, from about 350 to about 650 MPa, from about 350 to about 700 MPa, from about 350 to about 750 MPa, from about 350 to about 800 MPa, from about 350 to about 850 MPa, from about 350 to about 900 MPa, from about 350 to about 950 MPa and from about 350 to about 1000 MPa, from about 400 to about 1000 MPa, from about 450 to about 1000 MPa, from about 500 to about 1000 MPa, from about 550 to about 1000 MPa, from about 600 to about 1000 MPa, from about 650 to about 1000 MPa, from about 700 to about 1000 MPa, from about 750 to about 1000 MPa, from about 800 to about 1000 MPa, from about 850 to about 1000 MPa, from about 900 to about 1000 MPa, from about 950 to about 1000 MPa, from about 500 to about 550 MPa, from about 500 to about 600 MPa, from about 500 to about 650 MPa, from about 500 to about 700 MPa, from about 500 to about 750 MPa, from about 500 to about 800 MPa, from about 550 to about 800 MPa, from about 600 to about 800 MPa, from about 650 to about 800 MPa, from about 700 to about 800 MPa, from about 750 to about 800 MPa, from about 400 to about 800 MPa, from about 400 to about 750 MPa, from about 400 to about 700 MPa, from about 400 to about 650 MPa, from about 400 to about 600 MPa, from about 450 to about 800 MPa, from about 450 to about 750 MPa, from about 450 to about 700 MPa, from about 450 to about 650 MPa, from about 450 to about 600 MPa, from about 500 to about 800 MPa, from about 500 to about 750 MPa, from about 500 to about 700 MPa, from about 500 to about 650 MPa, from about 500 to about 600 MPa, from about 525 to about 675 MPa, from about 550 to about 650 MPa and from about 575 to about 625 MPa). Preferably the treatment pressure is at least about 350, 400, 450, 500 or 600 MPa.

In an alternative embodiment, preferably where the composition comprises a probiotic organism, the treatment pressure is selected from at least about 500, 510, 520, 530, 540, 550, 560, 570, 580, 590, 600, 610, 620, 630, 640, 650, 660, 670, 680, 690 and 700 MPa, and useful ranges may be selected between any of these values (for example, from about 500 to about 550 MPa, from about 500 to about 600 MPa, from about 500 to about 650 MPa, from about 500 to about 700 MPa, from about 550 to about 700 MPa, from about 600 to about 700 MPa, from about 650 to about 700 MPa and from about 550 to about 650 MPa). Preferably the treatment pressure is at least about 550, 600 or 650 MPa.

In one embodiment the pH of the composition when it is subjected to the pressure treatment is less than about 5.0, preferably less than about 4.6, more preferably about 3.0 to about 4.6, most preferably about 3.5 to about 4.1.

In another embodiment the pH of the composition when it is subjected to the pressure treatment is at least about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0 or greater, and useful ranges may be selected between any of these values (for example, from about pH 3.0 to about 4.5, from about pH 3.0 to about 5.0, from about pH 3.0 to about 5.5, from about pH 3.0 to about 6.0, from about pH 3.0 to about 6.5, from about pH 3.0 to about 7.0, from about pH 3.0 to about 7.5, from about pH 3.0 to about 8.0, from about pH 3.1 to about 4.9, from about pH 3.2 to about 4.8, from about pH 3.3 to about 4.7, from about pH 3.4 to about 4.6, from about pH 3.5 to about 4.5, from about pH 3.6 to about 4.4, from about pH 3.7 to about 4.3, from about pH 3.8 to about 4.2 and from about pH 3.9 to about 4.1). Alternatively, in still another embodiment, the pH of the composition is adjusted before pressure treatment to a pH or within a pH range listed above.

In one embodiment the method is conducted at ambient temperature. Preferably the pressure treatment is conducted at a temperature of at least about 0, 4, 5, 10, 15, 20, 25, 30, 35, 40, 45, 50, 55 or 60 degrees Celsius, and useful ranges may be selected between any of these values (for example, from about 5 to about 40 degrees Celsius). In one embodiment the temperature is about 0 degrees Celsius to about 40 degrees Celsius. In another embodiment the temperature is about 4 degrees Celsius to about 25 degrees Celsius.

In one embodiment the treatment pressure may be applied for a treatment time of about 1 second to about 30 minutes. Preferably the treatment time is selected from about 1, 5, 10, 20, 30, 60, 90, 120, 150, 180, 210, 240, 270 or 300 seconds or about 0.5, 1, 1.5, 2, 2.5, 3, 3.5, 4, 4.5, 5, 6, 7, 8, 9, 10, 15, 20, 25, 30, 35, 40, 45, 50, 55 or 60 minutes, and useful ranges may be selected between any of these values (for example, from about 1 to about 10 minutes, from about 1 to about 5 minutes or from about 2 to about 4 minutes).

In another embodiment the treatment pressure is held substantially constant for the treatment time. In another embodiment the pressure is increased from ambient pressure (usually atmospheric pressure) to the treatment pressure and then returned to ambient pressure within the treatment time. Ambient pressure will usually be atmospheric pressure.

It should be understood that in one embodiment a treatment time of a period listed above is the time taken to increase the pressure from atmospheric pressure to the treatment pressure and then return the pressure to atmospheric pressure. Accordingly, in one embodiment a treatment time of 1 minute means that the pressure is increased from atmospheric pressure to the treatment pressure and then returned to atmospheric pressure within 1 minute.

It should be understood that in another embodiment a treatment time of a period listed above is the time that the pressure is held at the treatment pressure (the "hold time"). Accordingly, in one embodiment a treatment time of 1 minute means that the pressure is held at the treatment pressure for 1 minute. Therefore, a treatment time of 0 (or "no hold") in this embodiment means that the pressure is raised to the treatment pressure but not held, and the pressure is then returned to atmospheric pressure. In this embodiment, preferred treatment times include 0 (no hold), 0.5, 1, 1.5, 2, 2.5, 3, 3.5, 4, 4.5, 5, 5.5, 6, 6.5, 7, 7.5, 8, 8.5, 9, 9.5 and 10 minutes. Preferably the pressure is held for about 0, 0.5, 1, 1.5, 2, 2.5, 3, 3.5, 4, 4.5 or 5 minutes, or for about 0, 0.5, 1, 1.5, 2, 2.5 or 3 minutes, or for about 0 minutes.

In one alternative embodiment the total treatment time is less than about 0.5, 1, 1.5, 2, 2.5, 3, 3.5, 4, 4.5, 5, 5.5, 6, 6.5, 7, 7.5, 8, 8.5, 9, 9.5 or 10 minutes. That is, the time taken for the pressure to be raised from and returned to ambient pressure (usually atmospheric pressure) is less than about 0.5, 1, 1.5, 2, 2.5, 3, 3.5, 4, 4.5, 5, 5.5, 6, 6.5, 7, 7.5, 8, 8.5, 9, 9.5 or 10 minutes. Preferably less than about 8 minutes, preferably less than about 7 minutes, preferably less than about 6 minutes or preferably less than about 5 minutes.

In another embodiment the composition may be subjected to additional pressure treatments. The treatment pressure may be changed from one treatment pressure to another, without first returning to atmospheric pressure. Each pressure treatment may be conducted for a separate treatment time. Accordingly, in one embodiment the pressure is increased from ambient pressure to a first treatment pressure for a first treatment time and then the pressure is changed to a second treatment pressure for a second treatment time. Preferably the first treatment time is longer than the second treatment time. Preferably the first treatment is shorter than the second treatment time. In yet another embodiment the pressure is increased to a first treatment pressure and then changed to a second treatment pressure within the treatment time.

In one embodiment the composition is subjected to the treatment pressure before incorporation into a product. In another embodiment the composition is subjected to the treatment pressure after incorporation into a product. Accordingly, the method further comprises subjecting the composition to the treatment pressure before or after incorporating the composition into a product. In another embodiment the composition is subjected to the treatment pressure before packaging. In another embodiment the composition is subjected to the treatment pressure after packaging. Accordingly, the method further comprises subjecting the composition to the treatment pressure before or after packaging.

In one embodiment the composition further comprises a stabiliser. Preferred stabiliser a gum selected from locust bean gum, guar gum, xanthan gum, cassia gum, konjac flour, beta-glucan, tara gum, gum arabic, gellan gum, carboxymethylcellulose, methylcellulose, hydroxypropyl methylcellulose, tragacanth gum, karaya gum, gum acacia, chitosan, arabinoglactins, alginate, pectin, carrageenan, or psyllium, or a mixture thereof. Preferably the stabiliser is pectin or carboxymethylcellulose (CMC), or a mixture thereof.

In another embodiment the composition further comprises a hydrophobic ligand. Preferably the hydrophobic ligand is selected from palmitic acid, myristic acid, linoleic acid, conjugated linoleic acid (CLA), one or more phospholipids, one or more phosphatidylcholines, one or more sphingomyelins, one or more gangliosides, butyric acid, one or more omega-3 fatty acids (including but not limited to eicosapentaenoic acid (EPA) and docosahexaenoic acid (DHA)), one or more phytosterols, one or more phytosterol esters, one or more phytosterol acetates, one or more omega-6 fatty acids (including but not limited to fish oil), fat soluble hydrophobic vitamins (including vitamin A [retinol] and vitamin D), lycopene, or sodium dodecyl sulphate, or a mixture thereof. Preferably the pH of the composition in this embodiment is from about 5.0 to 8.0.

In still another embodiment the composition further comprises at least one additional source of bioactive protein, lipid, protein hydrolysate, lipid hydrolysate, or carbohydrate or mixture thereof including but not limited to the dairy protein compositions or dairy ingredients described above.

In yet another embodiment the composition further comprises at least one additional bioactive component selected from lactoferrin, lysozyme, one or more immunoglobulins (including one or more IgA, IgD, IgE, IgG or IgM, or a mixture thereof, or a plurality of one or more of IgA, IgD, IgE, IgG or IgM that are specific for different epitopes), glycomacropeptide, growth factors (including milk derived growth factors, including TGF β1 and TGF β2), a composition comprising at least about 1% w/w immunoglobulin, a product made by inoculating an animal to increase antibody levels (hyperimmune milk or hyperimmune colostrum), immune milk, or one or more probiotic factors, or a mixture thereof.

In another embodiment the composition further comprises at least one additional bioactive component selected from one or more non-polar lipids, one or more polar lipids such as one or more phospholipids, one or more sphingolipids, one or more gangliosides or one or more ceramides, or a mixture thereof.

In still another embodiment the composition further comprises at least about 1% w/w immunoglobulins wherein the immunoglobulins comprise one or more IgA, IgD, IgE, IgG or IgM, or a mixture thereof, or a plurality of one or more of IgA, IgD, IgE, IgG or IgM that are specific for different epitopes.

In one embodiment the composition is a food product. Preferably the food product is a beverage, preferably an acidified beverage or a carbonated beverage. Preferably the food product is a yogurt including set, stirred, flavoured, fruit and probiotic yoghurts, fromage frais, petit suisse, quarg, fermented food or drink, acidified drink or milk product. Preferably the food product is a jelly.

In one embodiment the treatment pressure is about 400, 500, 600 or 700 MPa and the treatment time is about no hold, 1, 2 or 3 minutes. In another embodiment the treatment pressure is about 350 to about 500 MPa and the treatment time is about 0 minutes to about 5 minutes. Preferably the composition or product is yoghurt.

In still another embodiment the treatment pressure is about 400 to about 700 MPa and the treatment time is about 0 minutes to about 5 minutes. Preferably the composition or product is a fermented drink.

In yet another embodiment the treatment pressure is about 400 to about 700 MPa and the treatment time is about 0 minutes to about 10 minutes. Preferably the composition or product is an acid drink, a liquid concentrate (including gels) or yoghurt.

In still another embodiment the treatment pressure is about 350 to about 800 MPa, the treatment time is about 0 minutes to about 10 minutes and the pH of the composition or product is about pH 3.0 to about pH 7.0.

In one embodiment the bioactive component is immunoglobulin or lactoferrin; the pH of the product or composition is about pH 3.0 to about 5.0, preferably about pH 3.8 to about 4.5, preferably about pH 4.1; the treatment pressure is about 550 to 650 MPa, preferably 600 MPa; and the treatment time is selected from no hold or 1, 2 or 3 minutes.

In another embodiment the bioactive component is lactoferrin and the pH of the product or composition is about pH 3.5 to 4.5, preferably pH 4.1, the treatment pressure is about 550 to 650 MPa, preferably 600 MPa and the treatment time is selected from no hold or 1, 2 or 3 minutes.

In yet another embodiment the bioactive composition is a colostrum MPC or colostrum WPC; the bioactive component is immunoglobulin, preferably IgG; the pH of the product or composition is about pH 3.5 to 7.0, preferably pH 3.5 to 5.0, preferably pH 4.1; the treatment pressure is about 550 to 650 MPa, preferably 600 MPa; and the treatment time is selected from no hold or 1, 2 or 3 minutes.

In still another embodiment the bioactive composition is a colostrum MPC or colostrum WPC; the bioactive component is lactoferrin; the pH of the product or composition is about pH 3.5 to 7.0, preferably pH 3.5 to 5.0, preferably pH 4.1; the treatment pressure is about 550 to 650 MPa, preferably 600 MPa; and the treatment time is selected from no hold or 1, 2 or 3 minutes.

In another embodiment the bioactive component is an immune milk or an immune milk protein concentrate or an immune milk whey protein concentrate; the pH of the product or composition is about pH 3.5 to 7.0, preferably pH 3.5 to 5.0, preferably pH 4.1; the treatment pressure is about 550 to 650 MPa, preferably 600 MPa; and the treatment time is selected from no hold or 1, 2 or 3 minutes.

In yet another embodiment the bioactive component is an immune milk or an immune milk protein concentrate or an immune milk whey protein concentrate; the bioactive component is immunoglobulin, preferably IgG; the pH of the product or composition is about pH 3.5 to 4.5, preferably pH 4.1; the treatment pressure is about 550 to 650 MPa, preferably 600 MPa; and the treatment time is selected from no hold or 1, 2 or 3 minutes.

In another embodiment the bioactive component is an immune milk or an immune milk protein concentrate or an immune milk whey protein concentrate; the bioactive component is lactoferrin; the pH of the product or composition is about pH 3.5 to 4.5, preferably pH 4.1; the treatment pressure is about 550 to 650 MPa, preferably 600 MPa; and the treatment time is selected from no hold or 1, 2 or 3 minutes.

In still another embodiment the bioactive component is one or more IgG, the treatment pressure is about 550 to 650 MPa, the pH is about 3.0 to 5.0, and hold time is about 0 or 1, 2 or 3 minutes.

In one embodiment the bioactive composition is a bioactive dairy protein composition, the bioactive component is IgG or lactoferrin, the pressure is about 350 to 650 MPa, preferably 350 to 550 MPa, the pH is about 3.2 to 4.5, and the hold time is about 0, 1, 2 or 3 minutes.

In yet another embodiment the bioactive composition is a colostrum MPC, the bioactive component is IgG, the pressure is about 350 to 650 MPa, the pH is about 3.2 to 4.5, and the hold time is about 0, 1, 2 or 3 minutes.

In another embodiment the bioactive composition is a colostrum MPC, the bioactive component is IgG, the pressure is about 550 to 650 MPa, the pH is about 3.8, and the hold time is about 0, 1, 2 or 3 minutes.

In still another embodiment the bioactive composition is a colostrum MPC, the bioactive component is IgG, the pressure is about 550 to 650 MPa, the pH is about 3.2 to 7.0, and the hold time is about 0, 1, 2 or 3 minutes.

In another embodiment the bioactive composition is a colostrum skim milk powder, the bioactive component is IgG, the pressure is about 350 to 650 MPa, the pH is about 3.2 to 5.5, and the hold time is about 0, 1, 2 or 3 minutes.

In a further embodiment the bioactive composition is a colostrum skim milk powder, the bioactive component is IgG, the pressure is about 550 to 650 MPa, the pH is about 3.2 to 5.5, and the hold time is about 0, 1, 2 or 3 minutes.

In yet another embodiment the bioactive composition is a colostrum whey, the bioactive component is IgG, the pressure is about 350 to 650 MPa, the pH is about 3.2 to 5.5, and the hold time is about 0, 1, 2 or 3 minutes.

In another embodiment the bioactive composition is a colostrum whey, the bioactive component is IgG, the pressure is about 550 to 650 MPa, the pH is about 3.2 to 5.5, and the hold time is about 0, 1, 2 or 3 minutes.

In still another embodiment the bioactive composition is a colostrum whey UF retentate, the bioactive component is IgG, the pressure is about 550 to 650 MPa, the pH is about 3.2 to 5.5, and the hold time is about 0, 1, 2 or 3 minutes.

In another embodiment the bioactive composition is a hyperimmune milk, hyperimmune milk protein concentrate or hyperimmune whey protein concentrate hyperimmune colostrum, hyperimmune colostrum milk protein concentrate or hyperimmune colostrum whey protein concentrate, the bioactive component is IgA, IgG, IgM or lactoferrin, the pressure is about 550 to 650 MPa, the pH is about 3.2 to 5.5, and the hold time is about 0, 1, 2 or 3 minutes.

In yet another embodiment the bioactive component is lactoferrin, the pressure is about 550 to 650 MPa, the pH is about 3.0 to 7.5 and the hold time is about 0, 1, 2 or 3 minutes.

In still yet another embodiment the bioactive component is TGF-β1 or TGF-β2, the pressure is about 550 to 650 MPa, the pH is about 3.0 to 8.0 and the hold time is about 0, 1, 2 or 3 minutes.

In another embodiment the bioactive composition is a yoghurt, the bioactive component is lactoferrin, the pressure is about 450 to 650 MPa, the pH is about 3.5 to 5.0 and the hold time is about 0, 1, 2 or 3 minutes.

In a further embodiment the bioactive composition is a beverage, the bioactive component is IgG, the pressure is about 550 to 650 MPa, the pH is about 3.0 to 5.0 and the hold time is about 0, 1, 2 or 3 minutes.

In another embodiment the bioactive composition is a jelly, the bioactive component is lactoferrin, the pressure is about 550 to 650 MPa, the pH is about 3.0 to 5.0 and the hold time is about 0, 1, 2 or 3 minutes.

In another aspect the present invention relates to a composition treated or produced according to a method of the invention. In still another aspect the present invention relates to a probiotic composition treated or produced according to a method of the invention.

In yet another aspect the present invention relates to use of a composition treated or produced according to a method of the invention in the manufacture of an edible product such as a food, drink, food additive, drink additive, dietary supplement, nutritional product, medical food, nutraceutical, medicament or pharmaceutical.

In a further aspect the present invention relates to a composition comprising or consisting essentially of one or more probiotic microorganisms selected from one or more *Lactobacillus acidophilus* strains, one or more *Lactobacillus delbrueckii* subsp. *bulgaricus* strains, one or more *Lactobacillus casei* strains, one or more *Lactobacillus crispatus* strains, one or more *Lactobacillus johnsonii* strains, one or more *Lactobacillus plantarum* strains, one or more *Lactobacillus reuteri* strains, one or more *Lactobacillus rhamnosus* strains, one or more *Lactobacillus salivarius* strains, one or more *Bifidiobacterium bifidum* strains, one or more *Bifidiobacterium breve* strains, one or more *Bifidobacterium infantis* strains, one or more *Bifidiobacterium animalis* subsp. *lactis* strains, one or more *Bifidobacterium longum* strains, or one or more *Streptococcus thermophilus* strains, or a mixture thereof, and treated according to a method of the invention.

In yet another aspect the present invention relates to a composition comprising or consisting essentially of one or more probiotic microorganisms selected from *Lactobacillus rhamnosus* HN001, *Bifidiobacterium animalis* subsp. *lactis* HN019, *Lactobacillus acidophilus* HN017, or *Lactobacillus rhamnosus* HN067, or a mixture thereof, and treated according to a method of the invention.

In another aspect the present invention relates to a composition comprising or consisting essentially of lactoferrin, lysozyme, one or more IgA, one or more IgD, one or more IgE, one or more IgG, one or more IgM, one or more growth factors, TGF β1, or TGF β2, or a mixture thereof, and treated according to a method of the invention. In yet another aspect the present invention relates to a composition comprising or consisting essentially of lactoferrin, one or more IgA, one or more IgG, one or more IgM, TGF β1, or TGF β2, or a mixture thereof, and treated according to a method of the invention.

In another aspect the present invention relates use of a composition of the invention in the manufacture of a food, drink, food additive, drink additive, dietary supplement, nutritional product, medical food, nutraceutical, medicament or pharmaceutical, preferably the use is for treating a subject in need thereof, preferably for stimulating the immune system of a subject in need thereof. Accordingly, in yet another aspect the present invention relates to a method of stimulating the immune system of a subject in need thereof comprising administration of a composition of the invention.

Other aspects of the present invention relate to a pressure-treated composition comprising about 0.1 mg/ml to 1000 mg/ml of lactoferrin and less than about 50,000 cfu/ml of microorganisms, a pressure-treated composition comprising about 1 mg/ml to 1000 mg/ml of lactoferrin and less than about 50,000 cfu/ml of microorganisms, a pressure-treated composition comprising about 0.1 mg/ml to 1000 mg/ml of IgG and less than about 50,000 cfu/ml of microorganisms, a pressure-treated composition comprising about 1 mg/ml to 1000 mg/ml of IgG and less than about 50,000 cfu/ml of microorganisms, a pressure-treated jelly comprising about 0.1 mg/ml to 1000 mg/ml of lactoferrin and less than about 50,000 cfu/ml of microorganisms; a pressure-treated yoghurt comprising about 0.1 mg/ml to 1000 mg/ml of lactoferrin and less than about 50,000 cfu/ml of microorganisms; a pressure-treated beverage comprising about 0.1 mg/ml to 1000 mg/ml of lactoferrin and less than about 50,000 cfu/ml of microorganisms; a pressure-treated jelly comprising about 1 mg/ml to 1000 mg/ml of lactoferrin and less than about 50,000 cfu/ml of microorganisms; a pressure-treated yoghurt comprising about 1 mg/ml to 1000 mg/ml of lactoferrin and less than about 50,000 cfu/ml of microorganisms; a pressure-treated beverage comprising about 1 mg/ml to 1000 mg/ml of lactoferrin and less than about 50,000 cfu/ml of microorganisms; a pressure-treated jelly comprising about 0.1 mg/ml to 1000 mg/ml of IgG and less than about 50,000 cfu/ml of microorganisms; a pressure-treated yoghurt comprising about 0.1 mg/ml to 1000 mg/ml of IgG and less than about 50,000 cfu/ml of microorganisms; a pressure-treated beverage comprising about 0.1 mg/ml to 1000 mg/ml of IgG and less than about 50,000 cfu/ml of microorganisms; a pressure-treated jelly comprising about 1 mg/ml to 1000 mg/ml of IgG and less than about 50,000 cfu/ml of microorganisms; a pressure-treated yoghurt comprising about 1 mg/ml to 1000 mg/ml of IgG and less than about 50,000 cfu/ml of microorganisms; a pressure-treated beverage comprising about 1 mg/ml to 1000 mg/ml of IgG and less than about 50,000 cfu/ml of microorganisms. The pH of such compositions and the pressure at which they have been treated may be selected from the ranges described above.

Still other aspects of the present invention relate to a pressure-treated composition comprising one or more non-viable probiotic microorganism cultures and less than about 50,000 cfu/ml of microorganisms; a pressure-treated composition comprising one or more non-viable probiotic microorganism cultures selected from the group consisting of one or more *Lactobacillus acidophilus* strains, one or more *Lactobacillus delbrueckii* subsp. *bulgaricus* strains, one or more *Lactobacillus casei* strains, one or more *Lactobacillus crispatus* strains, one or more *Lactobacillus johnsonii* strains, one or more *Lactobacillus plantarum* strains, one or more *Lactobacillus reuteri* strains, one or more *Lactobacillus rhamnosus* strains, one or more *Lactobacillus salivarius* strains, one or more *Bifidiobacterium bifidum* strains, one or more *Bifidiobacterium breve* strains, one or more *Bifidobacterium infantis* strains, one or more *Bifidiobacterium animalis* subsp. *lactis* strains, one or more *Bifidobacterium longum* strains, or one or more *Streptococcus thermophilus* strains, or a mixture thereof, and less than about 50,000 cfu/ml of microorganisms; a pressure-treated composition comprising one or more non-viable probiotic microorganism cultures selected from the group consisting of *Lactobacillus rhamnosus* HN001, *Bifidiobacterium animalis* subsp. *lactis* HN019, *Lactobacillus acidophilus* HN017, or *Lactobacillus rhamnosus* HN067, or a mixture thereof, and less than about 50,000 cfu/ml of microorganisms; and a pressure-treated composition comprising a non-viable culture of *Lactobacillus rhamnosus* HN001 and less than about 50,000 cfu/ml of microorganism. The pH of such compositions and the pressure at which they have been treated may be selected from the ranges described above.

The entire disclosures of all applications, patents and publications, cited above and below, if any, are hereby incorporated by reference.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

DETAILED DESCRIPTION OF THE INVENTION

1. Definitions

Figure 1:
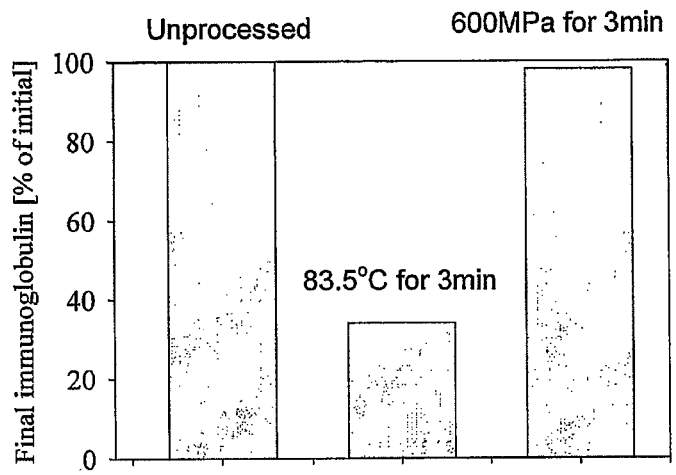
FIG. 1 is a graph showing the immunoglobulin fraction (as determined by HPLC) remaining in an acidified dairy beverage (3.6% protein at pH 3.5) after thermal processing of 83.5° C. held for 3 minutes compared to pressure processing of 600 MPa held for 3 minutes.
Figure 2A:
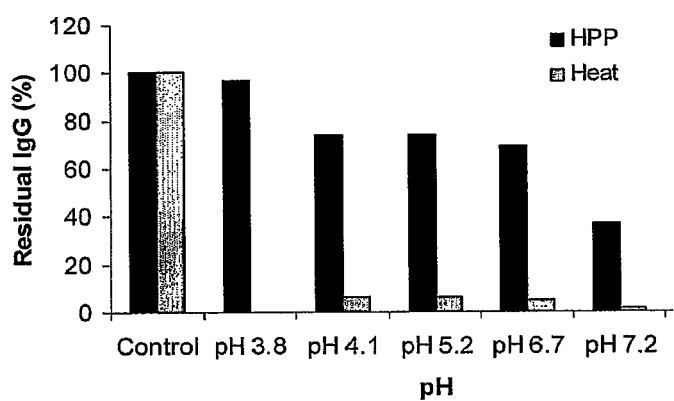
FIG. 2 is four graphs showing the effects of heat treatment (85° C./10 minutes) and pressure treatment (600 MPa/3 minutes hold) at varying pH on the IgG component of (A) a 6% w/v colostrum whey composition, (B) a 6% w/v colostrum whey UF retentate composition (ultrafiltration at 10 kDa), (C) a 6% w/v colostrum skim milk powder composition, and (D) a 6% w/v colostrum MPC composition.
Figure 2B:
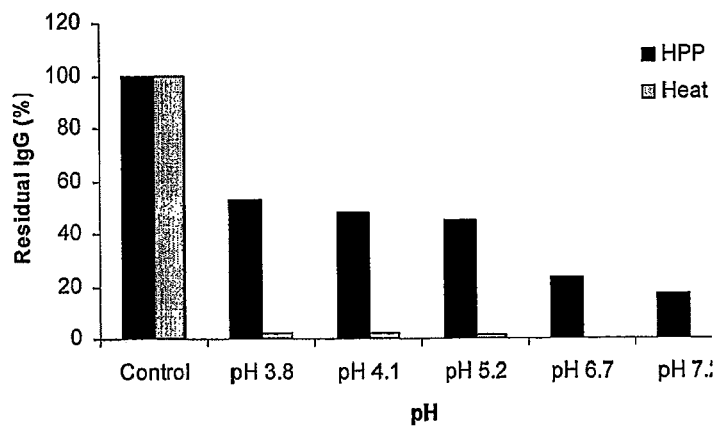
Figure 2C:
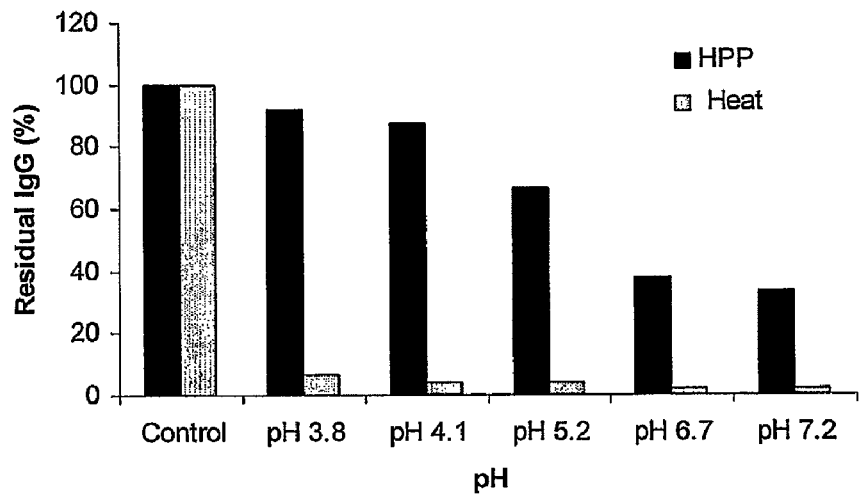
Figure 2D:
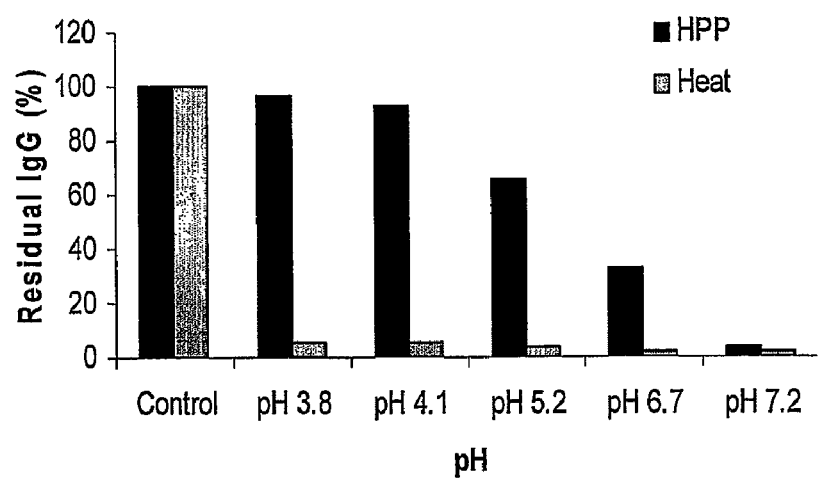

Reference to the "activity" of a bioactive component is intended to mean that the bioactive component is physiologically active when ingested and can have positive health benefits when administered by any means, preferably orally, to an animal, particularly mammals and including humans. Assessment of the activity of various bioactive components is described below.

Reference to retaining activity is intended to mean that a pressure treated bioactive component retains at least about 35, 40, 45, 50, 55, 60, 65, 70, 75, 80, 85, 90, 95, 99 or 100% of the activity of an untreated control, and useful ranges may be selected between any of these values (for example, from about 35 to about 100%, from about 50 to about 100%, from about 60 to about 100%, from about 70 to about 100%, from about 80 to about 100%, and from about 90 to about 100%).

In many instances, protein activity is associated with proper protein folding. Studies have shown that denaturation of natural and iron-loaded LF in UHT (ultra heat treated) milk affects its ability to bind various bacterial species and decreased its interaction capacity (Paulsson et al., 1993). Assessment of activity may therefore be made using analytical techniques that give an indication of the structural integrity of the proteins of interest. Immunoassays, such as radial immunodiffusion (RID), surface plasmon resonance (SPR), and affinity HPLC-MC require IgG to be intact before it can be measured. In enzyme-linked immunosorbent assay (ELISA), properly folded IgG or LF will be bound by the antibody and can be detected and visualised using enzyme-linked calorimetric agents. Information on loss of bioactivity of heat treated hyperimmunised dairy products is also given in Li, et al., 2003. Therefore, in some embodiments assessing the amount of properly folded protein before and after a pressure treatment will provide an assessment of retained activity. Preferably the bioactive component is a protein and retained activity is assessed by ELISA, flow cytometry, HPLC or BiaCore, as described below.

The bioactivity of lipids is associated with intact lipid or fatty acid molecules. Retorting lipid compositions (heat treatment at 120° C. for 15 minutes) causes excessive browning (colour change) of the composition due to degradation of phospholipids. For example, samples of 100 g NZMP phospholipid (PC 500) and 200 g anhydrous milk fat were pressure treated 600 MPa for 0 min, 600 MPa for 3 min of 600 MPa for 15 min or were retorted at 120° C. for 20 min. After retorting the phospholipid samples turned dark brown in colour (data not shown). In contrast pressure treated samples remained unaffected (data not shown). Preferably the bioactive component is a lipid and the retained activity is assessed by gas chromatography (GC) or HPLC.

The retained bioactivity of hydrolysates may be assessed by assessing the presence of desirable peptides using ELISA, flow cytometry, HPLC or BiaCore, as described below, or using in vitro or in vivo assays.

In one embodiment the activity is probiotic activity. Probiotic activity is described below. Preferably the bioactive component is a probiotic and probiotic activity is assessed by PBMC cytokine secretion assay.

The term "comprising" as used in this specification and claims means "consisting at least in part of". When interpreting statements in this specification and claims that include that term, the features, prefaced by that term in each statement, all need to be present but other features can also be present. Related terms such as "comprise" and "comprised" are to be interpreted in the same manner.

The terms "bioactive composition" or "bioactive product" or "bioactive ingredient" as used herein are intended to mean a composition or product or ingredient that is bioactive because of the presence of a bioactive component and includes food products and food ingredients. While the focus of preferred embodiments is on food products and food ingredients, particularly dairy products and dairy ingredients, it should be understood that the present invention is also useful for processing any composition or product or ingredient comprising a bioactive component including medical products that are not foods; for example, medical products for administration orally or parenterally. It should also be understood that in some embodiments the bioactive product will be an ingredient for incorporation into other products. Useful food products or food ingredients include any edible product or ingredient including beverages (including acidified beverages, carbonated beverages, consumable liquids and gels), nutraceuticals, and ingredients for use in such products. It should be understood that in some embodiments the food product will be an ingredient for incorporation into other products. The bioactive composition may also be a pharmaceutical composition.

The composition may be a liquid including a suspension of a solid in a liquid (including a paste or slurry). Examples of such compositions include a liquid concentrate (including gels), beverage (including acidified and carbonated beverages), jelly or yoghurt.

Examples of bioactive compositions include dairy protein compositions and dairy ingredients such as those described above.

The term "bioactive component" as used herein is intended to mean one or more proteins (including naturally occurring proteins or variants thereof such as recombinant, synthetic and modified proteins), one or more lipids (including modified lipids), one or more protein hydrolysates, one or more lipid hydrolysates, or one or more carbohydrates (including modified carbohydrates), or a mixture thereof that is physiologically active when ingested and can have positive health benefits when administered by any means, preferably orally, to an animal, particularly mammals and including humans. Preparation of recombinant proteins is described by Sambrook, et al., (1989).

Examples of bioactive proteins include but are not limited to lactoferrin, lysozyme, immunoglobulins (including IgA, IgD, IgE, IgG or IgM), glycomacropeptide, and growth factors (including milk derived growth factors including TGF β1 and TGF β2).

Examples of bioactive protein hydrolysates include but are not limited to casein hydrolysates, whey protein hydrolysates including hydrolysed whey, hydrolysed whey protein concentrate (WPC), hydrolysed whey protein isolate (WPI) or individual hydrolysed whey proteins such as alpha-lactalbumin, beta-lactoglobulin, proteose peptones, immunoglobulins (including IgA, IgD, IgE, IgG and IgM), glycomacropeptide, growth factors (such as TGF β1 and TGF β2), bovine serum albumin, lactoferrin, and lactoperoxidase. Other examples include those described in WO 99/65326 and WO 02/19837, ACE peptides isolated from whey hydrolysates (such as those described in WO 02/19837). Protein hydrolysates may be prepared as described below.

Examples of bioactive lipids include but are not limited non-polar lipids and polar lipids such as phospholipids, sphingolipids, gangliosides and ceramides.

Examples of bioactive compositions comprising at least one bioactive protein, lipid, protein hydrolysate, lipid hydrolysate, or carbohydrate, or a mixture thereof include dairy protein compositions and dairy ingredients such as those described above.

Further examples of a bioactive composition include but are not limited to a composition comprising at least about 1% w/w immunoglobulins wherein the immunoglobulins comprise one or more of IgA, IgD, IgE, IgG and IgM; a product made by inoculating an animal to increase antibody levels; and an immune milk.

The term "hold time" refers to a preferred embodiment where the treatment time is the time that the pressure is held at the treatment pressure. For example, a hold time of 1 minute means that the pressure is held at the treatment pressure for 1 minute. A hold time of 0 minutes (or "no hold") means that the pressure is raised to the treatment pressure but not held, and is then returned to ambient (usually atmospheric) pressure. In this embodiment, preferred treatment times include 0 (no hold), 0.5, 1, 1.5, 2, 2.5, 3, 3.5, 4, 4.5, 5, 5.5, 6, 6.5, 7, 7.5, 8, 8.5, 9, 9.5 and 10 minutes. It should be understood that although the pressure is not intentionally held at the treatment pressure, there may be a very short holding period (possibly several milliseconds) due to the nature of the equipment used. This very short holding period is unlikely to substantially affect the working of the method.

The term "keeping quality" as used herein is intended to mean the ability of a composition to resist the growth of unwanted microorganisms over time. Compositions that are not treated with heat or an acceptable alternative such as provided herein are unlikely to have a commercially acceptable keeping quality. Reference to maintaining keeping quality is intended to mean that a method of the invention is at least as effective as a heat treated control at extending the shelf-life of a pressure treated composition. Reference to increasing or increased, or improving or improved keeping quality is intended to mean that the ability of the composition to resist the growth of unwanted microorganisms over time is enhanced compared to an untreated composition. Enhanced keeping quality preferably leads to, for example, properties such as an extended shelf-life and an enhanced ability to withstand temperature variation. Temperature variation (such as removal from cold store) can induce growth of any residual bacteria.

Preferably the keeping quality is assessed with reference to the Aerobic Plate Count (APC). APC is a bacterial enumeration procedure used to estimate bacterial density in a sample and is otherwise known as Total Plate Count, Standard Plate Count or Total Viable Count. Samples are collected, blended, diluted, and plated in an agar medium suitable for detecting the bacteria studied (for example, food or dairy contaminants such as *Escherichia coli, Staphylococcus aureus, Salmonellae, Shigellae*, coliforms, yeasts and molds, mesophilic spores, thermophilic spores). The APC result is the number of colony forming units in one millilitre (cfu/ml) of sample that is plated and incubated for 72 hrs at 32° C. An APC of 50,000 cfu/ml or less is highly preferred for fresh dairy products that are not intended to contain viable cultures. Products having an APC of 50,000 cfu/ml or more are unlikely to have an acceptable keeping quality, unless the organism present is one that is particularly suited to the product—examples of this latter class of products include yoghurts or fermented products where a viable culture is desirable.

Accordingly, in one embodiment, a preferred method is one wherein the aerobic plate count (APC) after treatment is less than or equal to about 100,000, 75,000, 50,000, 25,000, 10,000, 5,000, 1,000, 100, or 10 colony forming units per millilitre (cfu/ml). Preferably the APC is less than about 50,000 cfu/ml.

The term "lactoferrin" refers to any non-glycosylated or glycosylated wild-type mammalian, preferably bovine or human, lactoferrin amino acid sequence or variants thereof.

The term "milk derived growth factor" is intended to include any growth factor found in mammalian milk or colostrum, preferably bovine milk or colostrum, such as Insulin-Like Growth Factor-I (IGF-I), Insulin-Like Growth Factor-II (IGF-II), Transforming Growth Factor-β1 (TGF-β1), Transforming Growth Factor-β2 (TGF-β2), Platelet-Derived Growth Factor (PDGF) and Heparin-Binding Growth Factors. Also included is Epidermal Growth Factor.

The term "pressure treatment" refers to ultra high-pressure (UHP) treatment. Such a treatment is generally accepted as using a pressure of at least 100 MPa. This is also known as "high pressure" treatment, "high hydrostatic pressure" (HHP) or "high pressure processing" (HPP). Products that have been "pressure treated" are those that have been subjected to UHP treatment; namely, pressure treatment at a pressure of at least 100 MPa, preferably pressure treatment at a pressure of at least about 350, 400, 450, 500, 600, 700 or 800 MPa (or otherwise within this range as described above).

The term "probiotic activity" refers to the ability of certain microorganisms to stimulate the immune system. Measuring the type and level of activity of a probiotic microorganism is known to those skilled in the art; see, for example, Mercenier et al. (2004), Leyer et al. (2004), or Cummings et al. (2004). Preferably probiotic activity is assessed by a PBMC cytokine secretion assay.

Reference to retaining probiotic activity is intended to mean an attenuated or killed probiotic microorganism still has useful probiotic activity. While the bacterial molecules responsible for mediating probiotic activity have not been clearly identified, possible candidate molecules include bacterial DNA motifs, surface proteins, small organic acids and cell wall components such as lipoteichoic acids and peptidoglycan. It is postulated that these interact with components of the host immune system to give an immuno-modulatory effect. Preferably, the retained activity is at least about 35, 40, 45, 50, 55, 60, 65, 70, 75, 80, 85, 90, 95, 99 or 100% of the activity of an untreated control, and useful ranges may be selected between any of these values (for example, from about 35 to about 100%, from about 50 to about 100%, from about 60 to about 100%, from about 70 to about 100%, from about 80 to about 100%, and from about 90 to about 100%).

The term "probiotic factor" refers to a bacterial molecule responsible for mediating probiotic activity, including but not limited to bacterial DNA motifs, surface proteins, small organic acids, or cell wall components such as lipoteichoic acids and peptidoglycan, or a mixture thereof. While, as noted above, these molecules have not been clearly identified, such molecules will be present if a probiotic organism is present.

The term "subject" refers to an animal, preferably a mammal, more preferably a mammalian companion animal or human. Preferred companion animals include cats, dogs and horses.

The term "unwanted microorganisms" refers to all microorganisms that may grow in a composition before pressure treatment. While such growth is undesirable, the presence of the microorganisms in states which do not grow, including non-viable, attenuated or dead microorganisms, may be of no consequence or may be desirable.

Reference to preventing the growth of unwanted microorganisms is intended to mean that the growth of microorganisms such as bacteria (including probiotic bacteria), fungi, molds, yeasts and algae is substantially reduced, delayed or eliminated. The microorganisms need not be responsible for spoilage or be pathogens. The growth of unwanted microorganisms can be assessed by visual inspection or by employing standard techniques that are known in the art, including but not limited to microscopy, staining, PCR, cell sorting and the like (see Lund, et al., 2000). Preferably the APC of the composition after pressure treatment is less than or equal to about 100,000, 75,000, 50,000, 25,000, 10,000, 5,000, 1,000, 100, or 10 cfu/ml, preferably less than about 50,000 cfu/ml As indicated above, compositions that are not heat treated or pressure treated are unlikely to have a commercially acceptable keeping quality. That is, the keeping quality of untreated compositions is usually unacceptable because no steps are taken to prevent the growth of unwanted microorganisms. Where such steps are taken, the keeping quality will be improved. A post-treatment aerobic plate count (APC) less than or equal to about 100,000, 75,000, 50,000, 25,000, 10,000, 5,000, 1,000, 100, or 10 colony forming units per millilitre (cfu/ml), preferably less than about 50,000 cfu/ml, will reduce, delay or eliminate the ability of any organisms present to have impact on keeping quality. In combination with low pH or refrigeration (storage at temperatures less than about 10° C., preferably less than about 4° C.) or both, their ability to affect keeping quality will be further reduced, delayed or eliminated.

In embodiments employing probiotic microorganisms, probiotic microorganism growth is unwanted but the presence of probiotic microorganisms is desirable. Accordingly, reference to preventing the growth of an unwanted microorganism in such embodiments is intended to mean that the growth of the probiotic microorganism is substantially reduced, delayed or eliminated. Preferably the pressure treatment will attenuate the probiotic microorganism, or more preferably, kill the probiotic microorganism, while retaining at least a desired level of probiotic activity.

In one embodiment the probiotic microorganism is an inactivated probiotic microorganism yet retains at least a desired level of probiotic activity. An inactivated probiotic microorganism may be non-viable, non-viable but still metabolically active, or dead, yet in all cases retain at least a desired level of probiotic activity.

In another embodiment the probiotic microorganism is an inactivated probiotic microorganism before pressure treatment. Pressure treatment in this embodiment prevents the growth of other unwanted microorganisms while retaining probiotic activity of the probiotic factors present.

The term "variant" refers to a naturally occurring (an allelic variant, for example) or non-naturally occurring (an artificially generated mutant, for example) protein that varies from the predominant wild-type amino acid sequence of the protein by the addition, deletion or substitution of one or more amino acids.

Generally, protein variants possess qualitative biological activity in common when assayed according to the examples below. Further, these variants may share at least about 50%, 55%, 60%, 65%, 70%, 75%, 80%, 85%, 90%, 95%, 96%, 97%, 98% or 99% sequence identity. Also included within the meaning of the term "variant" are homologues. A homologue is typically a protein from a different species but sharing substantially the same biological function or activity as the initial protein.

Preferred variant proteins preferably have at least about 70, 75, 80, 85, 90, 95 or 99% identity, preferably at least about 90, 95 or 99% identity to a wild type sequence. Identity can be determined by comparing a candidate amino acid sequences using the BLAST suite of programs (version 2.2.12; 28 Aug. 2005) (Tatusova, et al. (1999); McGinnis, et al. (2004)) that is publicly available from NCBI (ftp://ftp.ncbi.nih.gov/blast/).

Conservative substitutions of one or several amino acids without significantly altering biological activity are also useful. A skilled artisan will be aware of methods for making phenotypically silent amino acid substitutions (see for example Bowie et al., (1990)).

2. Pressure Treatment of Bioactive Compositions

The present inventors have shown it is possible to pressure treat bioactive compositions containing bioactive components under conditions that achieve a commercially useful keeping quality while maintaining the bioactivity of the bioactive components. In Example 1 below only 4% of the bioactivity of the bioactive component is lost after subjecting the bioactive product (a colostrum based beverage) to the treatment pressure, compared to a loss of over 50% of activity following thermal processing.

By way of example, bioactive compositions processed according to the invention may be delivered in pressure-treated products or ingredients; added to products or ingredients which are not subsequently heat-treated; or added to products or ingredients which are subsequently pressure-treated.

The present inventors have also shown that probiotic microorganisms subjected to pressure treatment retain the ability to stimulate the immune system. Therefore, pressure treatment is a useful tool to prevent growth of probiotic microorganisms in applications where such growth may be undesirable.

The present inventors have also shown that the use of a hydrophobic ligand enables bioactive components to be UHP treated at a pH of about 7.0, preferably at a pH of about 5.0 to 8.0, while retaining a higher level of activity than would be readily obtained in the absence of the ligand.

Accordingly, the present invention relates to methods for maintaining or increasing the keeping quality of a bioactive composition while retaining at least a desired level of activity of at least one bioactive component that is present in the composition, as described herein. The present invention also relates to methods of treating a probiotic composition to prevent the growth of the probiotic microorganism while retaining at least a desired level of probiotic activity.

While not intended to be limiting, a pressure treatment useful in a method of the invention preferably comprises the following steps:
(i) placing a composition to be pressure treated into the chamber of a pressure vessel and sealing the chamber;
(ii) raising the pressure in the chamber to a predetermined set pressure (the "treatment pressure");
(iii) holding the chamber at this pressure for a predetermined time, including less than one minute (the "hold time");
(iv) releasing the pressure from the chamber; and
(v) removing the pressure treated composition.

Such a protocol may be followed using batch or continuous processing equipment.

It should be understood that the pressure treatment may result in temperature fluctuations in the composition or product or ingredient during treatment. As such, references to preferred temperatures during pressure treatment refer to the temperature of the composition before the pressure is raised.

One method of predetermining a treatment pressure for use according to the present invention is to select a bioactive composition and subject it to a treatment pressure suitable for controlling one or more unwanted microorganisms. If necessary, the composition may be inoculated with an unwanted organism for the purposes of assessment. The retained bioactivity of the bioactive components may then be assessed as described herein.

Another method of predetermining a treatment pressure for use according to the present invention is to select a bioactive composition and subject it to a treatment pressure that retains at least a desired level of activity of at least one bioactive component. The growth of any unwanted microorganisms or the activity of a bioactive component or both may then be assessed as described herein, such as by assessing the post-treatment aerobic plate count. See for example, Lund, et al. (2000) for methods of assessing microorganism growth. These methods of assessment may also be employed by varying pH and hold times to determine the combination at which growth of unwanted organisms is prevented and at least a desired level of bioactivity is retained, as exemplified below.

3. Bioactivity of Bioactive Components

A bioactive composition treated or prepared according to the methods of the invention preferably retains at least a desired level of activity of at least one bioactive component. In one preferred embodiment, the desired level of activity is the same as or greater than the level of activity that may be retained if the bioactive composition is heat treated. For example, as shown in Example 1, heat treatment of a bioactive composition results in it retaining up to 34% of the activity of at least one bioactive component compared to the activity of the bioactive component in an untreated control. In contrast, a method of the invention may allow provision of a bioactive composition wherein at least about 34% or more of the activity of the bioactive component is retained, as shown in Example 1. For some bioactive components, heat treatment may be even more detrimental.

Therefore, and depending on the application, in one embodiment preferably at least about 35% of the activity of the at least one bioactive component is retained compared to the activity of the bioactive component in an untreated control. Preferably at least about 35, 40, 45, 50, 55, 60, 65, 70, 75, 80, 85, 90, 95, 96, 97, 98, 99 or 100% of the activity of the at least one bioactive component is retained, and preferred ranges may be selected between any of these values (for example, from about 70 to about 100%).

In an alternative embodiment, preferably the bioactive component retains at least about 10, 25, 50, 75, 100, 150, 200, 250, 300, 350, 400, 450, 500, 600, 700, 800, 900 or 1000% more activity than a heat treated bioactive component, and preferred ranges may be selected between any of these values (for example, from about 100 to about 400%).

The bioactivity of a bioactive component before and after pressure treatment according to the invention may be measured by known methods for assaying for a selected activity of a selected bioactive component, such as those described above and below.

Examples of accepted methods for measuring bioactivity include but are not limited to HPLC, cell-based assays, enzyme-based assays, ELISA assays, flow cytometry assays (that are becoming an accepted alternative to ELISA), radio-immune assays and in vivo assays using animal models.

For example, accepted methods for measuring the bioactivity of lactoferrin include but are not limited to chromatographic methods (Palmano et al, 2002), immunological techniques including ELISA (Desmazeaud, 1993) and biosensor immunoassays (Indyk et al, 2005).

The bioactivity of immunoglobulins and growth factors may be measured as described in the examples below.

Measuring the type and level of bioactivity of a probiotic microorganism is known to those skilled in the art. See, for example, Mercenier et al. (2004), Leyer et al. (2004), Cummings et al. (2004), and the PBMC cytokine secretion assay described below.

4. Bioactive Compositions

Milk is not only a complete source of nutrients for the neonate, but also provides a rich source of physiologically bioactive components and as such has been referred to as 'natures' 'pharmacy'. In addition to providing complete nutrition, milk also has vital roles in the development, protection and repair of the young. Healthy adults usually only require the nutritional benefits of milk, but in conditions of chronic ailments the bioactivities derived from milk have more to offer in terms of both prevention and treatment of illness. Preferably the milk is sheep, goat, pig, mouse, water buffalo, camel, yak, horse, donkey, llama, bovine or human milk, and most preferably bovine milk. Dairy protein is known to be immuno-stimulatory.

Colostrum is the pre-milk produced immediately after birth before standard milk production begins. Prime colostrum from cows is obtained within the first six hours after calving but colostrum can be collected within the first two days following calving. Prime colostrum typically contains more than twice the milk solids and four times the protein found in milk from the same cow obtained after about forty-eight hours later. The concentrations of digestive enzymes, immunoglobulins (including IgA, IgD, IgE, IgG and IgM), cytokines, interferons, growth factors, glycoproteins, proline-rich peptides and vitamins A, D, E and K are all higher in prime colostrum compared to standard milk. Colostrum milk protein concentrates (MPC) and colostrum whey protein concentrates (WPC) may be prepared as described by Elfstrand et al., 2002.

Milk and colostrum derivatives and methods of their manufacture are known in the art. Such derivatives are generally obtained by a combination centrifugation (for fat removal), casein precipitation (with acid or enzymes), filtration (to remove lactose, minerals and water, or optionally to remove proteins), chromatography (to purify protein components) and include recombined or fresh whole milk, recombined or fresh skim milk, reconstituted whole or skim milk powder, skim milk concentrate, skim milk isolate, whole or skim milk powder, skim milk retentate, concentrated milk, buttermilk, ultrafiltered milk retentate, milk protein concentrate (MPC), milk protein isolate (MPI), calcium depleted milk protein concentrate, calcium depleted milk protein isolate, low fat milk, low fat milk protein concentrate, low fat milk protein isolate, colostrum, a colostrum fraction, colostrum protein concentrate (CPC), colostrum milk protein concentrate, colostrum milk protein isolate, colostrum whey, colostrum whey protein concentrate, colostrum whey protein isolate, an immunoglobulin fraction from colostrum, whey, whey protein concentrate (WPC), whey protein isolate (WPI), sweet whey, lactic acid whey, mineral acid whey, reconstituted whey powder, a composition derived from any milk or colostrum processing stream, a composition derived from the retentate or permeate obtained by ultrafiltration or microfiltration of any milk or colostrum processing stream, or a composition derived from the breakthrough or adsorbed fractions obtained by chromatographic separation of any milk or colostrum processing stream, or a full or partial hydrolysate of any of these compositions, and or a mixture thereof. See for example the Dairy Processing Handbook (Tetra Pak Processing Systems, Lund, Sweden, 1995). Other such derivatives include the dairy protein compositions and dairy ingredients described above.

The proteins found in milk include immunoglobulins (including IgA, IgD, IgE, IgG and IgM), growth factors, bovine serum albumin (BSA), alpha-lactalbumin, beta-lactoglobulin and a large number of caseins, all of which are phosphoproteins. These proteins, with the exception of casein, are also present in whey. Milk is known to contain a variety of mitogenic proteins and proteins which may be involved directly in bone remodeling. Growth factors (IGF—Insulin-like Growth Factor, TGF—Transforming Growth Factor etc), immunoglobulins (including IgA, IgD, IgE, IgG and IgM), BSA and some beta lactoglobulin are recovered from milk or whey by cation exchange chromatography. Some growth factors are recovered as neutral proteins. Caseinoglycomacropeptide (CGMP) is an acidic protein fraction recoverable by anion exchange. Osteopontin is a highly phosphorylated and glycosylated protein found in all body fluids (including milk).

CGMP is a peptide released from kappa-casein during the rennet-mediated casein coagulation step (through the action of chymosin) of the cheese making process and is found in the whey fraction which is known as Sweet Whey or Cheese Whey. CGMP is sometimes referred to simply as GMP (glycomacropeptide). Cheese whey proteins consist of 15% to 20% CGMP. CGMP has been put forward as one of the bone health promoting components of milk, as reported in WO 00/49885.

Lactic acid whey is produced by fermentation with lactic acid bacteria or direct addition of lactic acid during the manufacture of caseinate or cottage and ricotta cheeses. Mineral acid whey is produced by addition of mineral acids during caseinate manufacture. Lactic acid whey and mineral acid whey do not contain CGMP. The basis of these two processes is to lower pH to about 4.6 to cause casein to precipitate as opposed to using the action of chymosin to cause precipitation. Therefore any milk products that have not been exposed to chymosin will not contain CGMP.

Whey is a by-product of cheese or casein manufacture, and the protein products derived from whey may be classified on the basis of their protein content, including whey protein concentrates (WPC) containing at least 30% protein, to whey protein isolates (WPI) containing at least 90% protein (Huffman, 1996; IDF, 1998). Membrane ultrafiltration and diafiltration is typically used in the manufacture of such products to concentrate and purify the whey protein to 25-35% solids before drying, and the protein concentrate derived from the membrane filtration step is known in the art as retentate. Whey protein is a collective term encompassing several individual proteins (including but not limited to alpha-lactalbumin, beta-lactoglobulin, proteose peptones, immunoglobulins (including IgA, IgD, IgE, IgG and IgM), glycomacropeptide, growth factors (such as TGF β1 and TGF β2), bovine serum albumin, lactoferrin, and lactoperoxidase) and in the present invention may include whey protein collectively or fractions thereof. Methods suitable for the commercial production of whey are described by Zadow (1992) and Sienkiewicz et al (1990). Methods for producing WPCs and WPIs are known in the art and discussed in the US Dairy Export Council Reference Manual for U.S. Whey and Lactose Products, Chapter 7: Whey Products—Definition, Composition, Functions; Page, J., Meyer, D., Haines, B., Lagrange, V., and Kenney, A. (Eds), American Dairy Products Institute, Elmhurst, Ill., USA, (June 2004) (also available on-line at http://www.usdec.orglfiles/pdfs/US08D_04.pdf). See also the Dairy Processing Handbook (Tetra Pak Processing Systems, Lund, Sweden, 1995). Whey protein is known to be immuno-stimulatory.

Hyperimmune milk and hyperimmune colostrum are made by immunising pregnant milk producing mammals with antigens from pathogens to raise specific antibodies in the colostrum and milk (see Korhonen, et al., 2000 for a review of such methods). Protein concentrates of hyperimmune products may be prepared according to the known methods referenced above. Hyperimmune milk and hyperimmune colostrum are known to be immuno-stimulatory (Korhonen, et al., 2000). Hyperimmune milk and hyperimmune colostrum may be processed like ordinary milk and colostrum to produce derivatives such as hyperimmune milk protein concentrate, hyperimmune milk protein isolate, hyperimmune whey, hyperimmune whey protein concentrate, hyperimmune whey protein isolate, hyperimmune colostrum, hyperimmune colostrum milk protein concentrate, hyperimmune colostrum milk protein isolate, hyperimmune colostrum whey, hyperimmune colostrum whey protein concentrate, or hyperimmune colostrum whey protein isolate, or a mixture thereof.

Lactoferrin is an 80 kDa iron-binding glycoprotein present in mammalian milk and colostrum. Lactoferrin concentration in bovine milk and colostrum is approximately 0.2 mg/ml and 1.5 mg/ml, respectively. It has multiple postulated biological roles, including regulation of iron metabolism, immune function, and embryonic development. Lactoferrin has anti-microbial activity against a range of pathogens including Gram positive and Gram negative bacteria, yeasts, and fungi. The anti-microbial effects of lactoferrin are based on its capability of binding iron, which is essential for the growth of the pathogens. Lactoferrin also inhibits the replication of several viruses and increases the susceptibility of some bacteria to antibiotics and lysozyme by binding to the lipid A component of lipopolysaccharides on bacterial membranes.

Lactoferrin may be isolated from milk by cation exchange chromatography followed by ultrafiltration and diafiltration. In addition to wild-type lactoferrin itself, useful variants also include bovine lactoferrin variants bLf-a and bLf-b (Tsuji, et al. (1989); Yoshida, et al. (1991)). Further useful variants include glycosylated and aglycosyl forms of lactoferrin (Pierce, et al. (1991); Metz-Boutigue, et al. (1984); van Veen, et al. (2004)) and glycosylation mutants (having variant points of glycosylation or variant glycosyl side chains). Useful lactoferrin fragments include the N-lobe and C-lobe fragments (Baker, et al., 2002) and any other lactoferrin polypeptides that retain a lactoferrin binding pocket, such as truncated lactoferrin polypeptides. Variants or fragments of lactoferrin may also be generated by known synthetic methods (see Kimmerlin, et al., 2005, for example). Alternatively, lactoferrin polypeptides or functional variants or fragments thereof can be produced by well established synthetic Fmoc chemistry as described for human kaliocin-1 and the lactoferricin derived peptide by Viejo-Diaz et al., (2003); and bovine lactoferricin peptide described by Nguyen et al., (2005); and lactoferrampin and shorter fragments described by van der Kraan et al., (2004).

The following is an exemplary procedure for isolating lactoferrin from bovine milk. Fresh skim milk (7 L, pH 6.5) is passed through a 300 ml column of S Sepharose Fast Flow equilibrated in milli Q water, at a flow rate of 5 ml/min and at 4° C. Unbound protein is washed through with 2.5 bed volumes of water and bound protein eluted stepwise with approximately 2.5 bed volumes each of 0.1 M, 0.35 M, and 1.0 M sodium chloride. Lactoferrin eluting as a discreet pink band in 1 M sodium chloride is collected as a single fraction and dialysed against milli Q water followed by freeze-drying. The freeze-dried powder is dissolved in 25 mM sodium phosphate buffer, pH 6.5 and subjected to chromatography on S Sepharose Fast Flow with a sodium chloride gradient to 1 M in the above buffer and at a flow rate of 3 ml/min. Fractions containing lactoferrin of sufficient purity as determined by gel electrophoresis and reversed phase HPLC are combined, dialyzed and freeze-dried. Final purification of lactoferrin is accomplished by gel filtration on Sephacryl 300 in 80 mM dipotassium phosphate, pH 8.6, containing 0.15 M potassium chloride. Selected fractions are combined, dialyzed against milli Q water, and freeze-dried. The purity of this preparation is greater than 95% as indicated by HPLC analysis and by the spectral ratio values (280 nm/465 μm) of ~19 or less for the iron saturated form of lactoferrin.

Hydrolysates can be prepared by selecting suitable enzymes with known specificity of cleavage, such as trypsin or chymotrypsin, and controlling/limiting proteolysis by pH, temperature, time of incubation and enzyme to substrate ratio. Refinement of such isolated peptides can be made using specific endopeptidases. In general, SDS-PAGE may be used to estimate the degree of hydrolysis by comparison of the hydrolysate to a molecular weight standard. Size exclusion chromatography may be used to separate various species within a hydrolysate and to estimate a molecular weight distribution profile. Protein hydrolysates, particularly dairy protein hydrolysates, are known to be immuno-stimulatory.

By way of example, compositions or products processed according to the invention may be delivered in pressure-treated products or ingredients; added to products or ingredients which are not subsequently heat-treated; or added to products or ingredients which are subsequently pressure-treated.

In order to reduce unwanted effects on proteins present in compositions treated according to the invention, it may be desirable in some embodiments where the composition is a liquid to add a stabiliser. For example, to stabilise any casein present in the composition. Accordingly, in one embodiment the composition further comprises a stabiliser such as a gum selected from locust bean gum, guar gum, xanthan gum, cassia gum, konjac flour, beta-glucan, tara gum, gum arabic, gellan gum, carboxymethylcellulose, methylcellulose, hydroxypropyl methylcellulose, tragacanth gum, karaya gum, gum acacia, chitosan, arabinoglactins, alginate, pectin, carrageenan, or psyllium or a mixture thereof. Preferably the stabiliser is pectin or carboxymethylcellulose (CMC). Preferably a composition to be treated according to the methods of the invention comprises about 0.01, 0.05, 0.1, 0.15, 0.2, 0.25, 0.3, 0.35% w/v or more of a stabiliser, as required.

To stabilise bioactive components at about neutral pH, in some embodiments it may be desirable to include in the composition one or more hydrophobic ligands. The presence of a hydrophobic ligand allows a bioactive component to be pressure treated at a pH of about 7.0, preferably at a pH of about 5.0 to 8.0, while retaining a higher level of activity than would be readily obtained in the absence of the ligand. Without wishing to be bound by theory, it is believed these ligands bind hydrophobic pockets in the bioactive components, reducing their sensitivity to denaturation during pressure treatment. Accordingly, in some embodiments it may be desirable that the composition further comprises one or more hydrophobic ligands selected from palmitic acid, myristic acid, linoleic acid, conjugated linoleic acid (CLA), one or more phospholipids, one or more phosphatidylcholines, one or more sphingomyelins, one or more gangliosides, butyric acid, one or more omega-3 fatty acids (including but not limited to eicosapentaenoic acid (EPA) and docosahexaenoic acid (DHA)), one or more phytosterols, one or more phytosterol esters, one or more phytosterol acetates, one or more omega-6 fatty acids (including but not limited to fish oil), fat soluble hydrophobic vitamins (including vitamin A [retinol] and vitamin D), lycopene, or sodium dodecyl sulphate, or a mixture thereof. Preferably the pH of the composition in this embodiment is from about 5.0 to 8.0.

Examples of product formulations useful herein include beverages (including acidified beverages and carbonated beverages), yoghurts and jellies. Such products may be formulated as described below and assessed as described above and in the examples. Accordingly, the present invention also relates to a pressure-treated composition comprising about 0.1 mg/ml to 1000 mg/ml of lactoferrin and less than about 50,000 cfu/ml of microorganisms and a pressure-treated composition comprising about 1 mg/ml to 1000 mg/ml of lactoferrin and less than about 50,000 cfu/ml of microorganisms. The present invention also relates to a pressure-treated composition comprising about 0.1 mg/ml to 1000 mg/ml of IgG and less than about 50,000 cfu/ml of microorganisms and a pressure-treated composition comprising about 1 mg/ml to 1000 mg/ml of IgG and less than about 50,000 cfu/ml of microorganisms. The composition may be a pressure-treated jelly, a pressure-treated yoghurt or a pressure-treated beverage. Lactoferrin or IgG concentration and microbial enumeration may be determined by the methods described herein.

The present invention also relates to a pressure-treated composition comprising one or more non-viable probiotic microorganism cultures and less than about 50,000 cfu/ml of microorganisms, as described above. Microbial enumeration may be determined by the methods described herein. In one embodiment the composition comprises at least about 0.1 mg/ml, preferably about 0.1, 0.5, 1, 2, 3, 4, 5, 10, 20, 30, 40, 50, 60, 70, 80, 90, 100, 200, 200, 400, 500, 600, 700, 800, 900, or 1000 mg/ml of the bioactive component, and useful ranges may be selected between any of these values (for example, from about 0.1 to 1000 mg/ml, from about 1 to 1000 mg/ml, from about 2 to 1000 mg/ml, from about 3 to 1000 mg/ml, from about 4 to 1000 mg/ml, from about 5 to 1000 mg/ml, and from about 10 to 1000 mg/ml).

Various aspects of the invention will now be illustrated in non-limiting ways by reference to the following examples.

EXAMPLES

All dairy products were obtained from Fonterra Co-operative Group Limited, New Zealand. For heat treatments, 4 ml samples were transferred into 8 ml Wheaton glass screw-capped vials and allowed to equilibrate at 30° C. for about 5-10 min then immersed in an oil bath maintained at 75° C. or 85° C. and rocked for 10 min followed by rapid cooling in ice for 10 min. Samples were stored at 4° C. until analysis.

Analysis of Samples

Qualitative and quantitative changes in IgG, IgM, IgA, growth factors or LF as a result of heat or pressure treatments were assessed using one or more techniques selected from visual observation, polyacrylamide gel electrophoresis (PAGE), HPLC, BiaCore or ELISA. Samples were also tested for presence of various microorganisms (including Aerobic plate count, coliform count, yeast and mold count, mesophilic spore count, thermophilic spore count and others) before and after pressure treatment.

1. ELISA: Performed according to the manufacturer's instructions.
2. HPLC-MC: Samples were diluted and analysed by the HPLC-MC method described by Copestake, et al., 2006. Casein can interfere with the accuracy of IgG analysed by HPLC. To establish a more accurate and reproducible method of IgG analysis for colostrum products, high performance liquid chromatography with prior casein removal (HPLC-minus casein or HPLC-MC) is used. This ensures that the IgG concentration measured more closely reflects measurements by RID, SPR and other immunoassay methods.
3. BiaCore: Samples were diluted in PBS buffer and analysed using a BiaCore instrument as described by Indyk & Filonzi (2005). Quantitation was obtained by reference to a standard curve constructed using high purity bovine lactoferrin or IgG.
4. PAGE: Sodium dodecyl sulfate (SDS) PAGE of selected samples (reduced and non-reduced) was performed using methods as described by Manderson et al (1998).
5. Microbiological Analysis: Microbial analysis was conducted according to NZTM2 43.1—APC (Aerobic Plate Count); NZTM2 48.1—coliform count; NZTM2 60.1—thermophilic count; NZTM2 59.1—mesophilic spore count; and NZTM2 61.1—yeast and mould count, all from NZTM 2: New Zealand Dairy Industry Microbiological Methods Manual (Publishing Solutions Limited, P.O. Box 983, Wellington, New Zealand), based on International Dairy Federation and AOAC International methods.

Example 1

Solution Containing Colostrum Ingredient

A colostrum milk protein concentrate powder (Fonterra Co-operative Group Limited) containing 80% protein (and 6.6% immunoglobulins) was made up with water and the pH adjusted to 3.5 with lactic acid to yield a 3.6% protein solution. A sample of the solution was then heat-treated or pressure-treated at 83.5° C. or 600 MPa respectively, held for 3 minutes, and the quantity of immunoglobulins in the treated beverages was measured by HPLC and compared to the quantity in the unprocessed solution. The results are shown in FIG. 1. An HPP unit from Stansted Fluid Power Ltd, UK was used for all examples.

Example 2

Solutions Containing Colostrum MPC Ingredient

Colostrum MPC was dissolved in a 0.3% w/v pectin solution to prepare a 6% w/v stock solution of colostrum MPC. Samples of the colostrum stock solution were acidified to a range of pH values and either heat-processed at 85° C. and held for 10 min or pressure-processed as described below. The residual immunoglobulin G (IgG) of each heat- and pressure-processed sample relative to an unprocessed control at the same pH was measured by HPLC-MC. The solutions were also challenged with coliforms, yeast and mould and were enumerated for these organisms following pressure treatment at 600 MPa.

At pH 3.3, a colostrum sample pressure-processed at 400 MPa and held for 3 min had 67% IgG remaining, compared to 2% for heat-processed colostrum.

At pH 4.1, a colostrum sample pressure-processed at 600 MPa and held for 3 min had 37% IgG remaining, compared to 2% for heat-processed colostrum.

At pH 3.5, a colostrum sample pressure-processed at 600 MPa and held for 3 min had 34% IgG remaining, compared to 2% for heat-processed colostrum.

At pH 4.1, a colostrum sample pressure-processed at 500 MPa and held for 1 min had 91% IgG remaining, compared to 2% for heat-processed colostrum.

At pH 4.1, colostrum samples pressure-processed at 400 MPa, 500 MPa and 600 MPa without holding had 100% at 400 MPa, 91% at 500 MPa and 48% at 600 MPa IgG remaining, compared to 2% for heat-processed colostrum, as summarised in Table 1A. The microbial quality of these samples was compared and is summarised in Table 1A. The unprocessed control preparation had counts of $9 \times 10^3$ cfu/mL coliforms, an estimated 100 cfu/mL mesophilic spores and above $1 \times 10^6$ cfu/mL of both yeasts/moulds and colonies on an aerobic plate count (APC). In comparison, samples pressure processed at 500 MPa or 600 MPa without holding had no detectable coliforms or yeasts/moulds. At 600 MPa, no mesophilic spores or APC were detected. At 500 MPa, there were an estimated 20 cfu/mL mesophilic spores and 27 cfu/mL APC. At 400 MPa there were an estimated 40 cfu/mL mesophilic spores and 2100 cfu/mL APC.

The residual immunoglobulin activity and coliform and yeast and mould counts at 600 MPa across the pH range are shown in Table 1B.

TABLE 1A

Residual IgG and APC of HPP 6% w/v colostrum MPC samples (pH 4.1)

| Pressure | Residual IgG % | APC[cfu/mL] |
|---|---|---|
| Unprocessed | 100 | >1,000,000* |
| 400 MPa/no hold | 100 | 2100 |
| 500 MPa/no hold | 91 | 27 |
| 600 MPa/no hold | 48 | Not detected |

*measured before pH adjustment

TABLE 1B

Residual immunoglobulin activity and microorganism counts after pressure treatment at 600 MPa at various hold times and pH values.

| pH | Hold time (min) | IgG [%] | Coliform count [cfu/mL] | Yeast/mould count [cfu/mL] |
|---|---|---|---|---|
| 6.8 | Unprocessed | 100 | 18,000,000* | 300,000* |
| 3.3 | 0 | 40 | Not detected | Not detected |
|  | 1 | 33 | Not detected | Not detected |
|  | 2 | 33 | Not detected | Not detected |
|  | 3 | 35 | Not detected | Not detected |
| 3.5 | 0 | 45 | Not detected | Not detected |
|  | 1 | 36 | Not detected | Not detected |
|  | 2 | 36 | Not detected | Not detected |
|  | 3 | 34 | Not detected | Not detected |
| 3.8 | 0 | 55 | Not detected | Not detected |
|  | 1 | 40 | Not detected | Not detected |
|  | 2 | 38 | Not detected | Not detected |
|  | 3 | 34 | Not detected | Not detected |
| 4.1 | 0 | 48 | Not detected | Not detected |
|  | 1 | 64 | Not detected | Not detected |
|  | 2 | 40 | Not detected | Not detected |
|  | 3 | 37 | Not detected | Not detected |

*challenged

Example 3

Colostrum MPC Ingredient at Various pH

Colostrum samples from the stock solution of Example 2 were acidified to pH 3.5 to 4.1 and pressure processed at 400 to 600 MPa (no hold) and compared to a heat-processed preparation. In all cases approximately 2% residual IgG was retained after heat treatment, compared to 45-100% residual IgG retained after pressure treatment, with the highest residual IgG at the higher pH. The results are summarised in Table 2.

TABLE 2

Residual IgG (%) of heat-or pressure-processed 6% w/v colostrum MPC

| Pressure | pH 3.5 | pH 3.8 | pH 4.1 |
|---|---|---|---|
| Unprocessed | 100 | 100 | 100 |
| 85° C./10 min | 2 | 2 | 2 |
| 400 MPa/no hold | 75 | 92 | 100 |
| 500 MPa/no hold | 54 | 73 | 91 |
| 600 MPa/no hold | 45 | 56 | 48 |

Example 4

Effect of Various Ingredients

Colostrum solutions prepared from a section of colostrum ingredients at various pH values and subjected to heat (85° C./10 minutes) and pressure (600 MPa/3 minutes hold) treatments were analysed for residual IgG activity by HPLC-MC. The results are shown in FIG. 2 for (A) colostrum whey (CW), (B) colostrum whey UF retentate (CWUFR) (rennet whey subjected to ultrafiltration with a UF membrane having a 10 kDa molecular weight cut off), (C) colostrum skim milk powder, and (D) colostrum MPC. The amount of residual IgG in heat-treated preparations was consistently below 10%.

The colostrum whey UF retentate ingredient (FIG. 2B) showed greater losses of IgG after pressure treatment than solutions made from the other ingredients. However, at pH of 5.2 and below, useful IgG levels in pressure-treated colostrum skim milk powder preparations were still retained.

At pH of 5.2 and below, there is substantial retention of IgG in all the other pressure-treated preparations. In particular, at pH 4.1 and below for the preparations from colostrum skim milk powder (FIG. 2C) and colostrum MPC (FIG. 2D) and at pH 3.8 for the preparation from colostrum whey (FIG. 2A), the residual IgG is above about 90%. The residual IgG level at pH 6.7 for the colostrum whey (FIG. 2A) was also at a useful level (about 70%).

Example 5

Ingredients from Hyperimmune Colostrum

Two 7% w/v hyperimmune (HI) colostrum stock solutions were formulated, one from hyperimmune colostrum milk protein concentrate (HI-MPC) and one from hyperimmune colostrum whey protein concentrate (HI-WPC). Sample of these stock solutions were adjusted to pH 4.6 and subjected to a heat treatment of 85° C. held for 10 min or pressure treatments of 600 MPa without holding or 600 MPa held for 3 min. For enumeration of microorganisms, samples were stored for a week at ambient temperature before treatment and enumeration. The residual levels of a selection of bioactive proteins were measured, immunoglobulins IgG, IgA and IgM by ELISA, and lactoferrin BiaCore, as described earlier. The microorganisms were enumerated as aerobic plate counts (APC) and are shown in Table 3. After treatment of 400 MPa without holding, the APC was reduced by 4 logs for HI-MPC and 3 logs for HI-WPC. After treatment at 600 MPa held for 3 min, the APC was reduced by 5.8 logs for HI-MPC and >5.6 logs for HI-WPC.

Figure 3A:
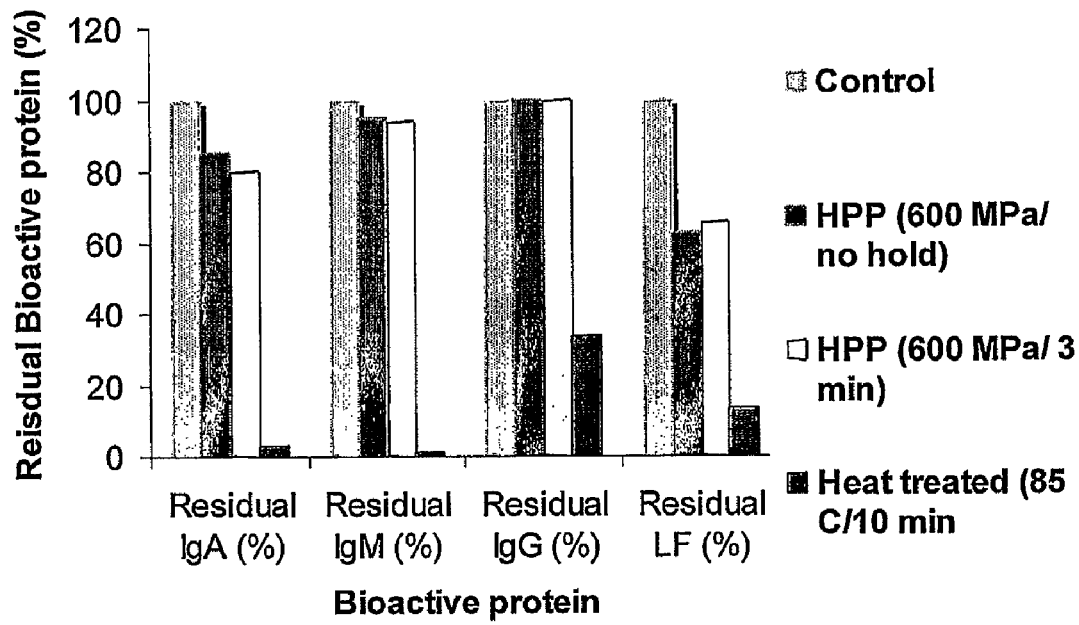
FIG. 3 is two graphs showing residual IgA, IgG, IgM and lactoferrin (LF) levels (%) in pressure treated (600 MPa/no hold and 600 MPa/3 minutes) and heat treated (85° C./10 minutes) samples of (A) a 7% w/v HI-MPC composition and (B) a 7% w/v HI-WPC composition. Results are expressed as a percentage of the IgA, IgG, IgM and lactoferrin levels of an untreated control sample.
Figure 3B:
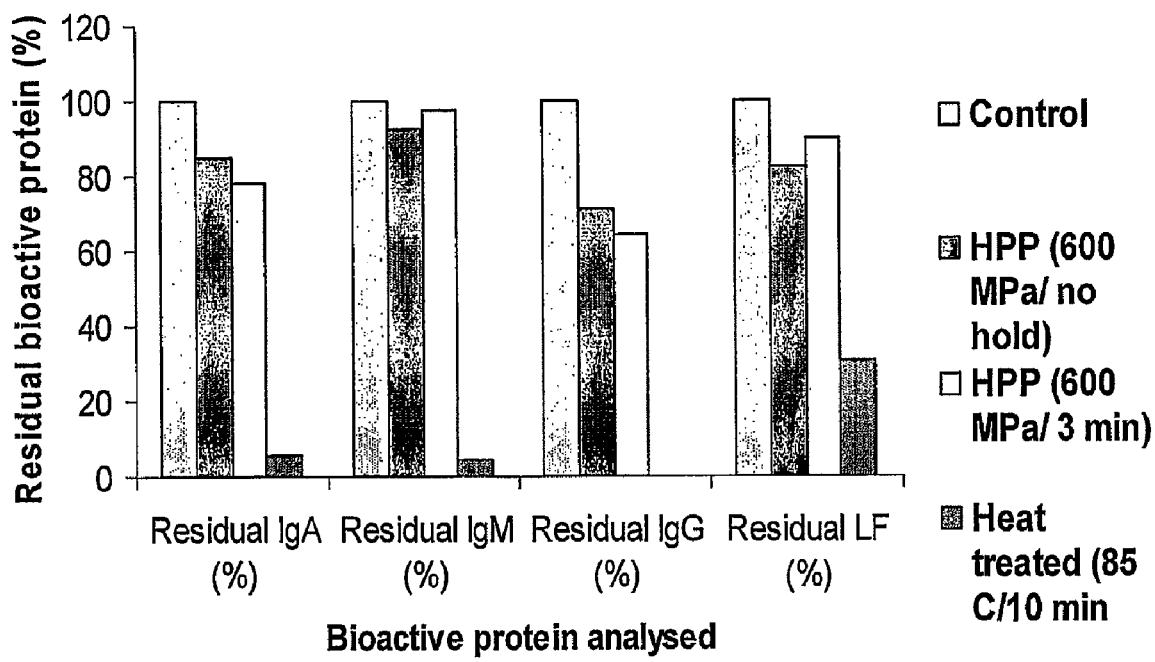

The treated samples were then held for 6 weeks at 20° C. and then further enumeration was done to assess the outgrowth of contaminating microorganisms. These results are shown in Table 4. The residual bioactive protein levels are shown in FIG. 3 (show all together at pH 4.1).

Very little (2-3%) residual IgA was left in the sample heat treated at 85° C. for 10 min. In contrast, pressure treated samples had much higher residual IgA activity (80-85% residual IgA).

An almost similar trend was seen for IgM, showing that only negligible amounts of residual IgM activity (~1% residual IgM remained) in the heat treated samples as compared to more than 95% residual IgM activity in the samples pressure treated at 600 MPa for no hold or 600 MPa for 3 min.

TABLE 3

APC [cfu/ml] of pressure and heat treated HI-MPC and HI-WPC

| Ingredient | Control | 400 MPa no hold | 600 MPa held 3 min. | 85° C. held 10 min |
|---|---|---|---|---|
| HI-MPC pH 4.6 | 18,000,000 | 460 | 30 | not done |
| HI-WPC pH 4.6 | 370,000 | 300 | none detected | not done |
| HI-MPC pH 6.9 | 18,000,000 | 25,000,000 | 54,000 | 7 |
| HI-WPC pH 6.9 | 370,000 | 1,600 | 20 | 2 |

TABLE 4

APC [cfu/ml] of the samples of Table 3 after 6 weeks at 20° C.

| Ingredient | Control | 400 MPa no hold | 600 MPa held 3 min. | 85° C. held 10 min |
|---|---|---|---|---|
| HI-MPC pH 4.6 | spoiled | 10 | 10 | 10 |
| HI-WPC pH 4.6 | spoiled | 20 | none detected | none detected |
| HI-MPC pH 6.9 | spoiled | spoiled | spoiled | spoiled |
| HI-WPC pH 6.9 | spoiled | spoiled | 50 | none detected |

Example 6

Effect of Low pH on Bioactivity

Figure 4A:
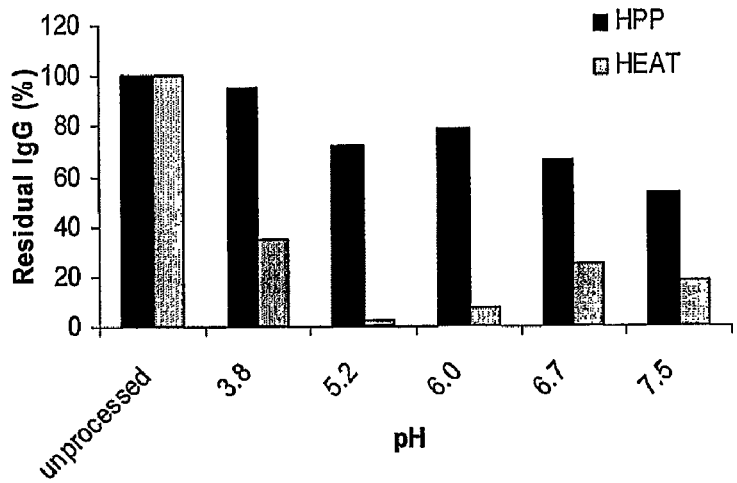
FIG. 4 is two graphs showing residual IgG and Lactoferrin (LF) levels in unprocessed, pressure treated (600 MPa/3 minutes) and heat treated (75° C./5 minutes) samples of a 7% w/v WPC composition.
Figure 4B:
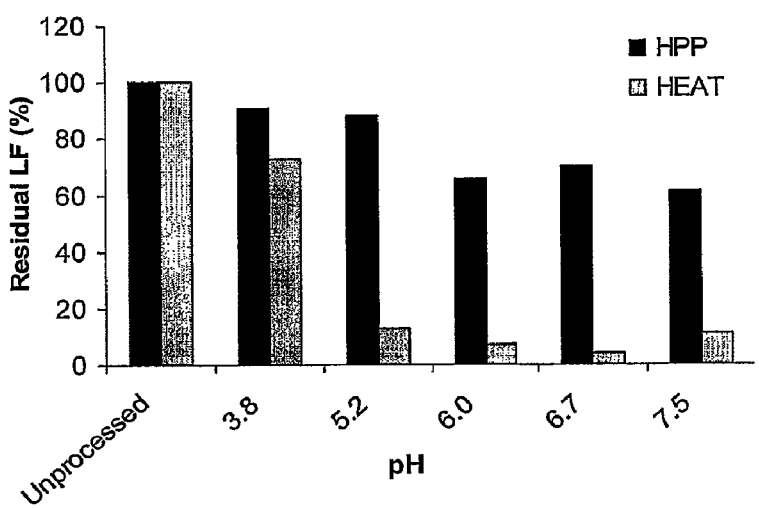

Solutions of 7% w/v commercial whey protein concentrate (WPC) were prepared by dissolving an appropriate quantity of WPC powder in Milli-Q water. The pH of each solution was separately adjusted to 3.8, 5.2, 6.0, 6.7 and 7.5 and the solutions were then pressure treated at 600 MPa held for 3 minutes or heat-treated at 75° C./held for 5 minutes and analysed for residual IgG and lactoferrin content using BiaCore method as described earlier. The results are presented in FIG. 4.

The residual IgG activity was in the range of 5 and 35% in the heat treated samples. In contrast, samples pressure treated at 600 MPa for 3 min (FIG. 4A) showed 50-95% residual IgG. The samples pressure treated at lower pH showed comparatively higher residual IgG compared to samples pressure treated at higher pH (e.g. pH 6.7 and above). Similarly, the residual lactoferrin activity in heat treated WPC solutions was 5 and 70 compared to 60-90% in the samples pressure treated at 600 MPa held for 3 minutes (FIG. 4B. Samples pressure treated at lower pH showed comparatively higher residual LF (%) compared to samples pressure treated at higher pH (e.g. pH 6.0 and above).

Example 7

Lactoferrin is Very Pressure Stable at pH 4.0

Figure 5:
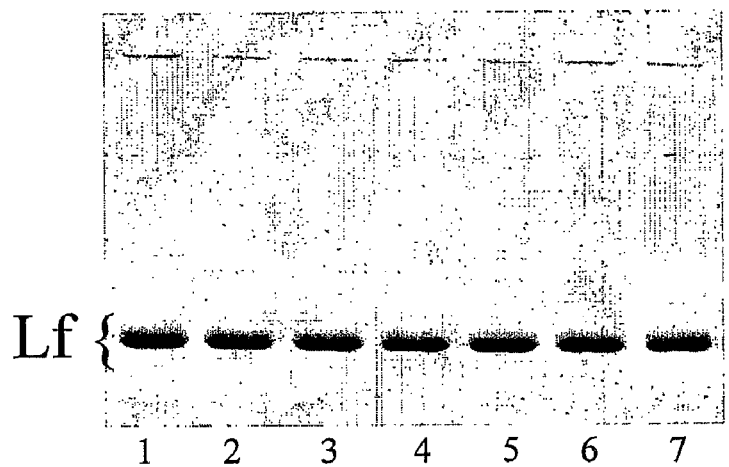
FIG. 5 is a graph showing residual LF levels in samples of a 6% w/v lactoferrin solution pressure treated as follows: (1) Control, (2) 600 MPa/5 min, (3) 600 MPa/15 min, (4) 600 MPa/30 min, (5) 600 MPa/45 min, (6) 75° C./5 min, (7) 85° C./5 min, and (8) 90° C./5 min.

The non-reducing SDS PAGE of dilute LF solutions (0.2% w/v, pH 4.0), pressure treated at 400 MPa between 5 and 50 min is shown in FIG. 5 (Lane 1: untreated control; Lane 2: 400 MPa/5 minutes; Lane 3: 400 MPa/10 minutes; Lane 4: 400 MPa/20 minutes; Lane 5: 400 MPa/30 minutes; Lane 6: 400 MPa/40 minutes; Lane 7: 400 MPa/50 minutes). The gel shows that the band intensity of LF before and after prolonged pressure treatment at 400 MPa remained largely unchanged. These results show that the LF is highly pressure resistant at this pressure, even if the solutions were pressure treated for an extended time.

Example 8

Solution Containing Lactoferrin at Various pH

Figure 6:
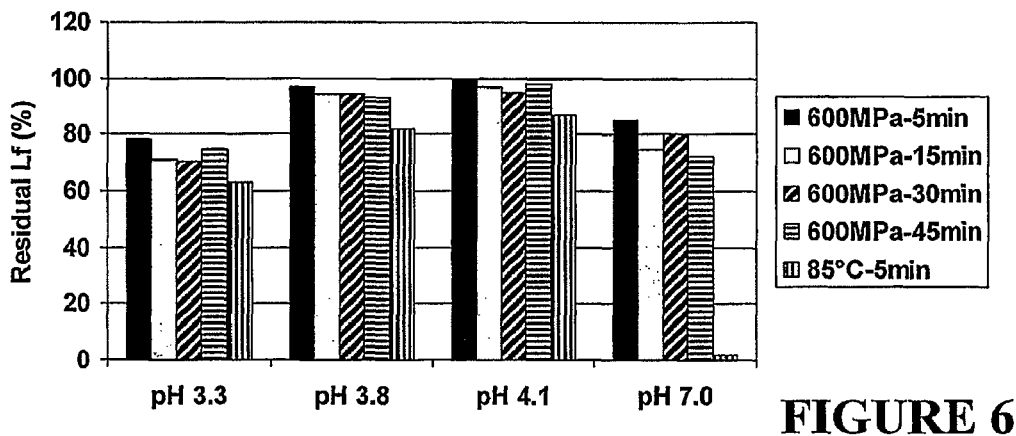
FIG. 6 is a graph showing residual LF levels (%) in samples of a 6% w/v lactoferrin solution that were pressure- or heat-treated at varying pH as follows: 600 MPa/5 min, 600 MPa/15 min, 600 MPa/30 min, 600 MPa/45 min, or 85° C./5 min. Results are expressed as a percentage of the lactoferrin levels of an untreated control sample.

Lactoferrin solutions (6% w/v) were prepared from lactoferrin powder dissolved in milli-Q water and stirred gently for 2-3 hours. The solutions were adjusted to pH 3.3, 3.8, 4.1 or 7.0 and either pressure treated (600 MPa held for up to 45 min) or heat treated (85° C. held for 5 min). The residual lactoferrin was measured by the BiaCore method and is shown in FIG. 6. The colour of a lactoferrin solution is indicative of the proteins iron-binding capacity, which may be adversely affected by processing. A 6% solution of native lactoferrin is approximately 15% iron-saturated and is a burnt orange colour, whereas an apo-lactoferrin solution that is 0% iron-saturated is colourless. The pressure-treated (600 MPa, held for 5 or 30 min) and heat-treated solutions (85° C. or 90° C. held for 10 min) were also compared on reducing and non-reducing SDS-PAGE at pH 3.8, 4.8 and 7.0.

At pH 7.0 there was little residual lactoferrin after heat treatment at 75° C. or above, held for 5 min. Samples heated over the pH range from 3.3 to 4.1 had showed higher residual lactoferrin (FIG. 6), but after pressure treatment at 600 MPa even for substantial hold times, the residual lactoferrin at the same pH values was consistently higher.

Heat treatment at 75° C. held for 5 min caused marked colour loss over the pH range 3.8-7.0 indicating loss of iron or oriented iron-binding in lactoferrin (Table 5) compared to an unprocessed control. Note that at pH 3.3, lactoferrin has a reduced capacity for iron binding. Heat treatment at 85° and above held for 5 min caused extensive loss of colour over the pH range. A thick precipitate formed at pH 7.0, indicating extensive denaturation of lactoferrin.

TABLE 5

Effect of heat treatment on native lactoferrin as a function of pH

| | pH: | | | | |
|---|---|---|---|---|---|
| Treatment Conditions: | 3.3 | 3.8 | 4.0 | 5.2 | 7.0 |
| Control | clear | ++ | ++ | +++ | +++ |
| 75° C./5 min | clear | almost clear | + | ++ | ++ |
| 85° C./5 min | clear | clear | Clear | clear | thick ppt |
| 90° C./5 min | clear | clear | Clear | clear | thick ppt |

"+" symbols indicate colour depth on visual inspection. Fewer "+" symbols indicate less iron binding.

In contrast, pressure treatment at 600 MPa held for up to 45 min caused no colour change or turbidity compared to unprocessed controls, except at pH 3.8 and 4.0, where colour was comparable to the solutions at higher pH (Table 6).

TABLE 6

Effect of pressure treatment on native lactoferrin as a function of pH

| | pH: | | | | |
|---|---|---|---|---|---|
| Treatment Conditions: | 3.3 | 3.8 | 4.0 | 5.2 | 7.0 |
| Control | clear | ++ | ++ | +++ | +++ |
| 600 MPa/5 min | clear | +++ | +++ | +++ | +++ |
| 600 MPa/10 min | clear | +++ | +++ | +++ | +++ |
| 600 MPa/30 min | clear | +++ | +++ | +++ | +++ |
| 600 MPa/45 min | clear | +++ | +++ | +++ | +++ |

"+" symbols indicate colour depth on visual inspection. Fewer "+" symbols indicate less iron binding.

On review of the SDS-PAGE gels referred to above (not shown), the heat-treated solutions showed evidence of polymerization and aggregation, either caught-up at the start of the resolving gel, within the stacking gel or as very large polymers that did not enter the gels at all. At pH 3.8 and 4.8, there was aggregated material that did not penetrate into the non-reducing gels and was absent in the reducing gel. This indicated that aggregation was due to heat-induced polymerisation. At pH 7 almost no measurable lactoferrin remained. In contrast the pressure-treated solutions showed almost no changes from the untreated controls.

The solutions of lactoferrin (6% w/v) adjusted at pH 3.3, 3.8, 4.0, 5.0, 6.0, 7.0 and 8.0 were also challenged with yeast and moulds and then pressure treated at 600 MPa for 0, 5 and 15 min. The enumeration of yeast and moulds in unprocessed control and pressure treated samples showed that the unprocessed control had 190,000 yeast and moulds counts (cfu/ml), whereas no yeast and moulds were detected in the pressure treated samples at all pressure treatment and all pH range studied.

Example 9

Solution Containing Growth Factors

A HI-WPC (7% w/v) solution was prepared by dissolving HI-WPC powder in Milli-Q water at pH 6.9. The solution was then either pressure treated at 600 MPa without holding or 600 MPa held for 3 minutes or was heat treated at 85° C. held for 10 min. The pressure treated and heat treated samples were analysed for two major bovine colostrum growth factors TGF β1 and TGF β2 compared to an unprocessed control.

Figure 7A:
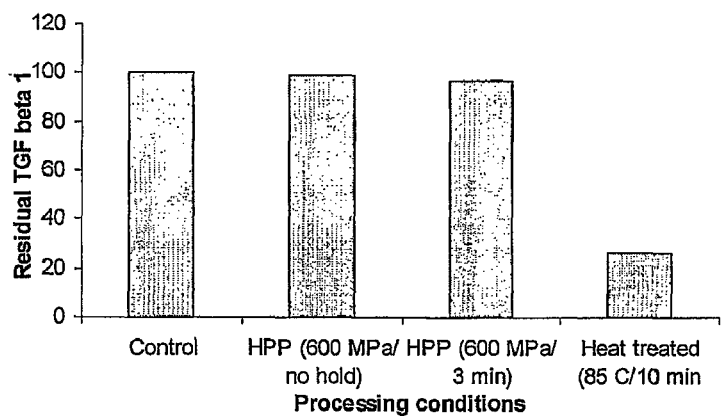
FIG. 7 is two graphs showing residual growth factor (TGF beta 1 and TGF beta 2) levels in heat or pressure treated samples of a 7% w/v solution of HI-WPC.
Figure 7B:
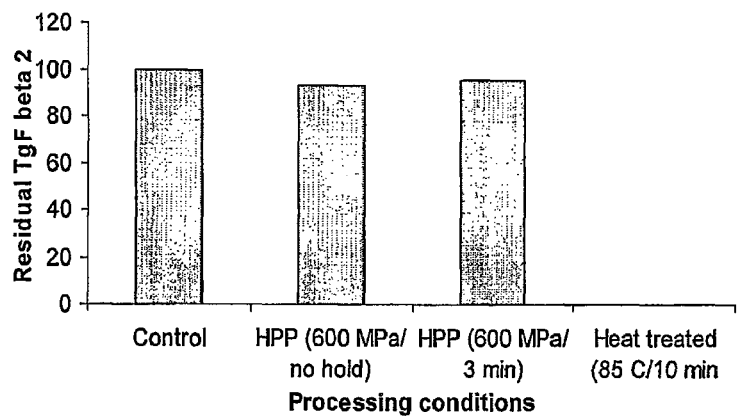

The results are presented in FIG. 7 (A) TGF β1 and (13) TGF β2. The heat-treated sample had 27% residual TGF β1 growth factor and no detectable TGF β2 growth factor. In contrast, the pressure processed samples held for 3 min had between 93-99% of both growth factors.

Example 10

Yogurt Containing Lactoferrin

Figure 8:
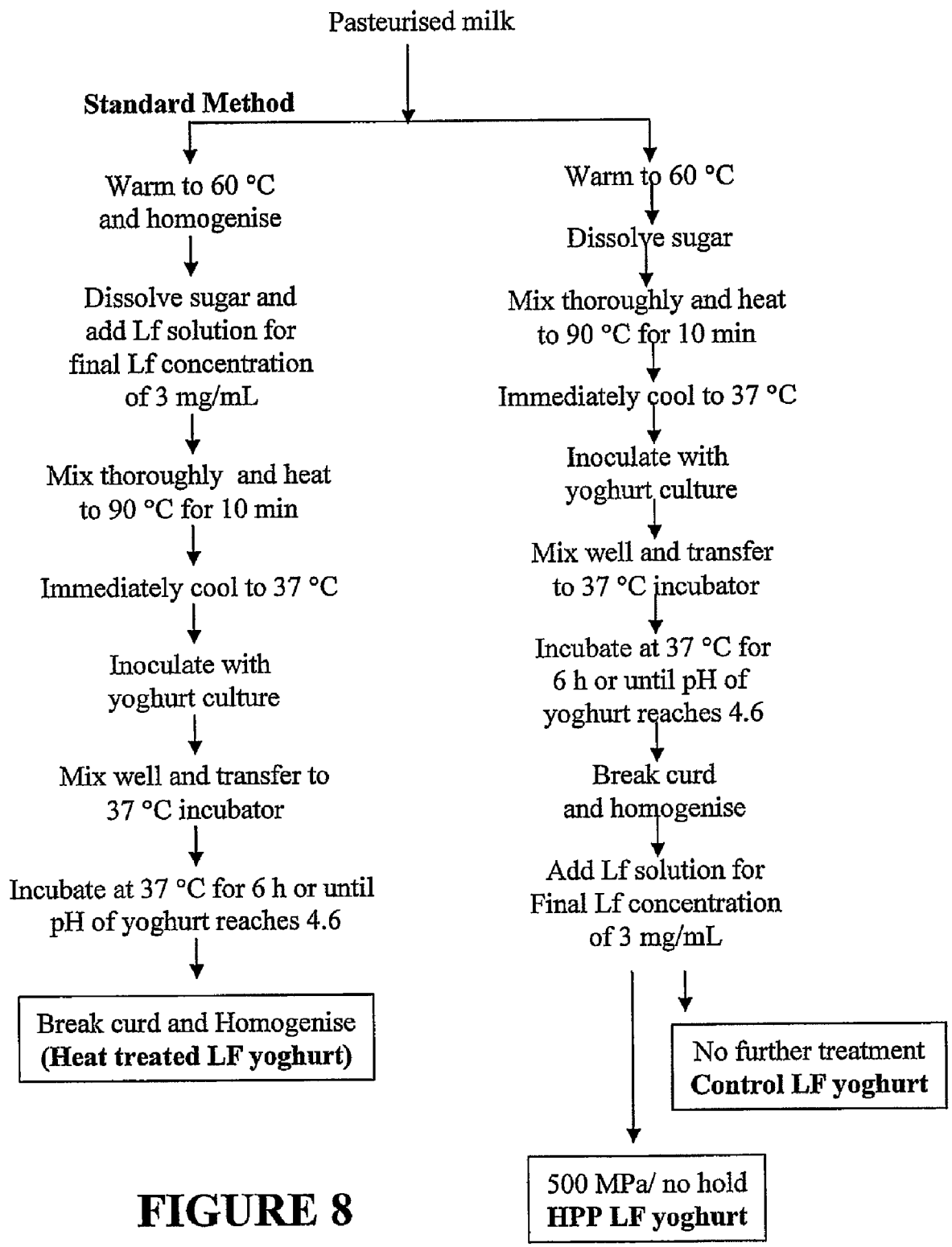
FIG. 8 is a flow chart summarising the manufacture of control LF yoghurt, heat treated LF yoghurt and HPP treated LF yoghurt.
Figure 9:
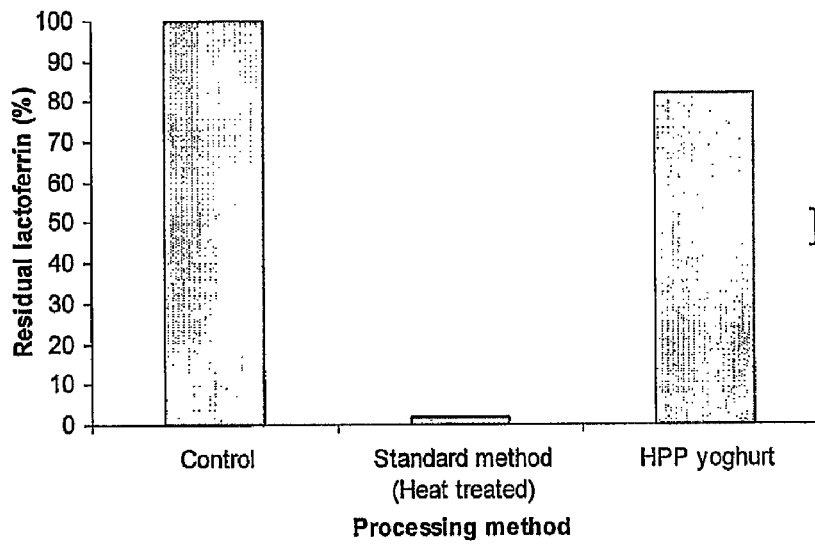
FIG. 9 is a graph showing residual LF levels in control, heat treated and HPP treated LF yoghurt.

Lactoferrin yoghurts were prepared by three different methods as shown in FIG. 8. In the first (standard yoghurt) lactoferrin was added to the milk before heat treatment, in the second (control), lactoferrin was added to the yoghurt after fermentation, and in the third (HPP method), lactoferrin was added to the yoghurt after fermentation, and the fortified yoghurt was pressure-treated at 500 MPa without holding. The final pH of the yoghurt was measured to be 4.50. The lactoferrin in the yoghurt was measured by the BiaCore method and the results are presented in FIG. 9. The standard heat-treated lactoferrin yoghurt had 1-2% residual lactoferrin activity, (relative to the control method). In contrast, the residual lactoferrin obtained by the pressure method was 80%. The pressure-treated yogurt was analysed for spoilage micro-organisms after 130 days storage at 4° C. There were no detectable coliforms, sixty colonies of mesophilic spores, and no detectable staphylococci, yeast or mould and approximately ten colonies on an aerobic plate count. In contrast, unprocessed control product was extensively spoiled within 21 days of preparation, with evidence of gas production and odour.

Example 11

Beverage Containing Immunoglobulin

Figure 11:
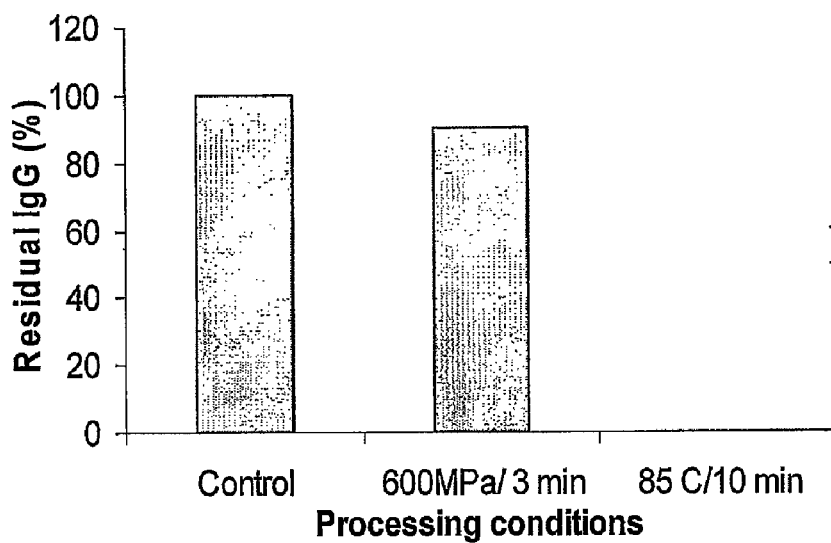
FIG. 11 is a graph showing residual IgG levels in a control acidic drink, heat treated acidic drink and HPP treated drink acidic drink.
Figures 10, 12:
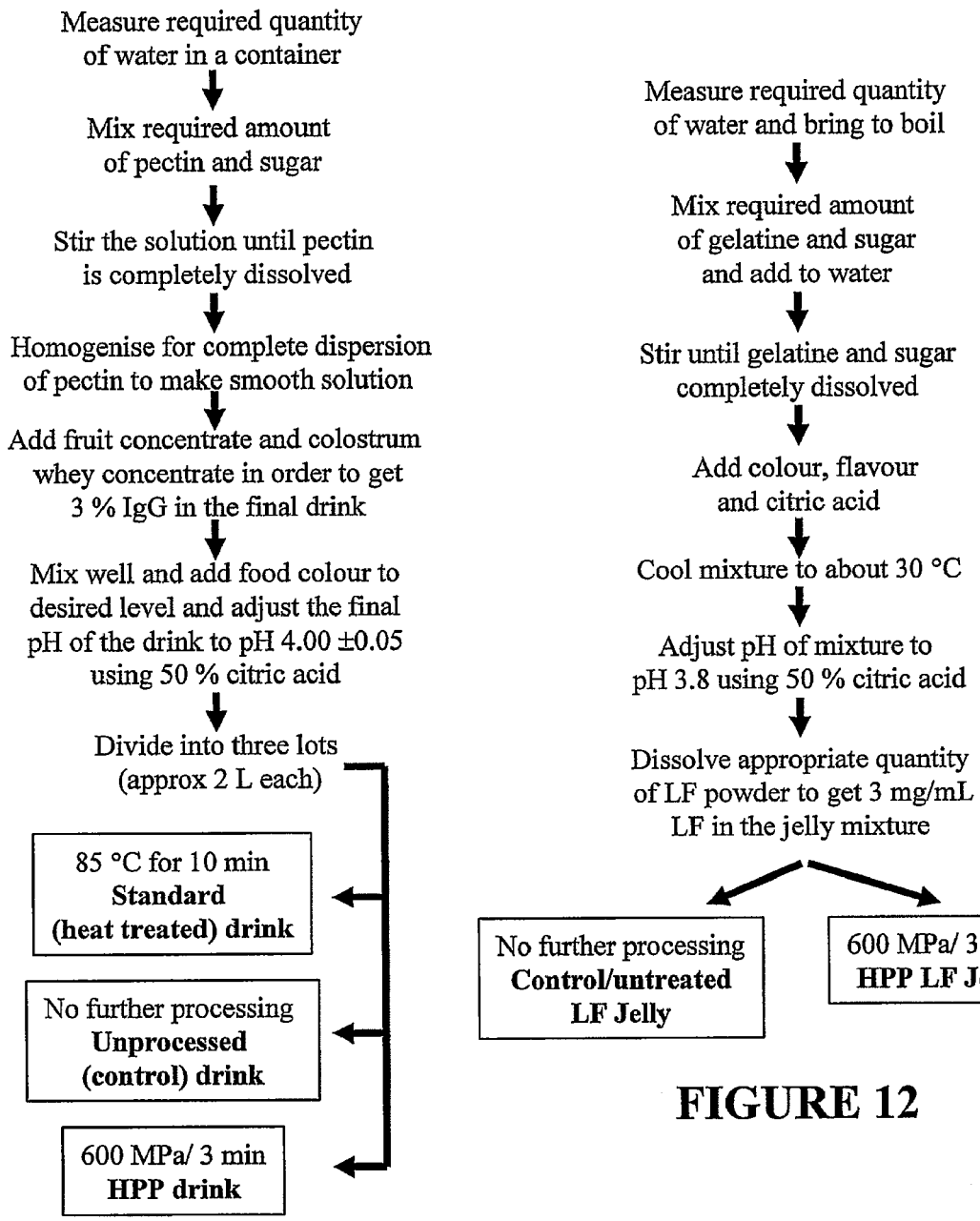
FIG. 10 is a flow chart summarising the manufacture of a standard (heat treated) acidic drink, an unprocessed (control) acidic drink and an HPP treated acidic drink.
FIG. 12 is a flow chart summarising the manufacture of control (untreated) LF jelly and HPP treated LF jelly.

An acidified beverage (pH 4.0) containing immunoglobulins (as 3% IgG) was prepared from a colostrum whey concentrate as shown in FIG. 10. The beverage was either heat-treated at 85° C. held for 10 min or pressure treated at 600 MPa held for 3 min and the residual IgG was measured by the HPLC-MC method relative to an unprocessed control. The results are presented in FIG. 11. The drinks prepared by the heat-treatment procedure had residual IgG that was below the limit of detection. In contrast, the drink prepared by pressure treatment retained ~90% residual IgG (%) compared to the control. The product pressure processed at 500 MPa without holding was analysed for spoilage micro-organisms after 130 days storage at 4° C. There were no detectable coliforms, two colonies of mesophilic spores, and no detectable staphylococci, yeast or mould or colonies on an aerobic plate count. In contrast, unprocessed control product was extensively spoiled within 21 days of preparation, with evidence of gas production and odour.

Example 12

Jelly Containing Lactoferrin

Figure 13:
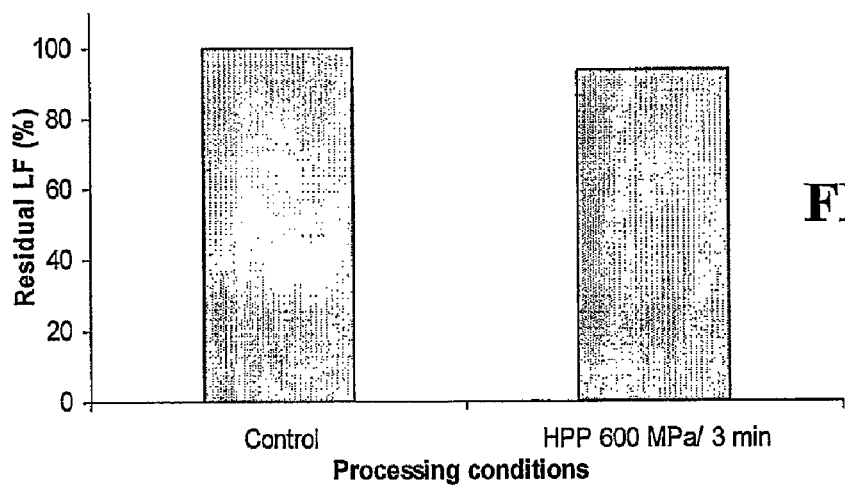
FIG. 13 is a graph showing residual LF levels in control and HPP treated LF jelly.

A fruit-flavoured jelly product at pH 3.8 was prepared from lactoferrin powder as described in FIG. 12. The jelly was pressure-treated at 600 MPa for 3 min and the residual lactoferrin was compared to an unprocessed control sample by the BiaCore method. The results are shown in FIG. 13. The pressure-treated jelly had above 90% residual lactoferrin compared to the unprocessed control jelly. The product was analysed for spoilage micro-organisms after 130 days refrigerated storage. There were no detectable coliforms, mesophilic spores, staphylococci, yeast or mould or colonies on an aerobic plate count. In contrast, unprocessed control product was extensively spoiled within 21 days of preparation, with evidence of gas production and odour.

Example 13

Pressure Treatment of a Probiotic Microorganism

Preparation of Inactivated Probiotic Bacteria

A culture of *Lactobacillus rhamnosus* HN001 (AGAL deposit number NM97/09514, 18 Aug. 1997; Cross et al., 2002) was grown for 18 h in 1 litre of a static NM broth at 37° C. from a 1:100 inoculum. After growth of the culture all steps were performed on ice, unless mentioned otherwise. This culture was washed once in cold sterile PBS and resuspended in this in a final total volume of 150 ml to give an estimated concentration of approximately $2 \times 10^{10}$ cfu/ml. This was then aliquoted into five equivalent 30 ml aliquots in 50 ml Stansted polypropylene centrifuge tubes and three of these were treated as follows:

Heat inactivated HN001—A 30 ml aliquot of cells was incubated in a water bath at 70° C. for 30 minutes, and then transferred to ice. A 500 µl aliquot of these heat treated cells was then further diluted in PBS to give an estimated concentration of $1 \times 10^8$ cfu/ml, and 400 µl aliquots of this were dispensed into Nalgene cryogenic vials, snap frozen in liquid nitrogen and stored at −80° C. until required for PBMC cytokine secretion assays.

Live HN001—A 30 ml aliquot of cells were treated exactly as for the heat-treated cells, except they received no heat treatment.

UHP inactivated HN001—A 30 ml aliquot of cells was further aliquoted into Beckman centrifuge tubes, sealed and pressure treated at 600 MPa with a 3 min hold time. After treatment the pressure treated cells were pooled into a fresh Stansted 50 ml centrifuge tube and mixed. A 500 µl aliquot of these cells was then further diluted in PBS to give an estimated concentration of $1 \times 10^8$ cfu/ml, and 400 µl aliquots of this were dispensed into Nalgene cryogenic vials, snap frozen in liquid nitrogen and stored at −80° C. until required for PBMC cytokine secretion assays.

Human Peripheral Blood Mononuclear Cell (PBMC) Preparation

Whole blood samples were collected from volunteers after gaining informed consent. Blood was collected into tubes that contained heparin as an anti-coagulant. 20 ml aliquots were transferred to sterile 50 ml tubes, and diluted to 35 ml with sterile PBS. Diluted blood was underlayed with approximately 15 ml Ficoll-Hypaque (d=1.077), and centrifuged at 1500 g for 20 min at room temperature. PBMC were harvested from the interface, whereas red blood cells and neutrophils settled to the pellet. The collected PBMC were diluted at least 2-fold in PBS, and then pelleted by centrifugation (5 min at 400 g). Following aspiration of the supernatant, PBMC were resuspended in 50 ml PBS and an aliquot removed for counting. Based on the cell count, the remaining PBMC were diluted in RPMI 1640/10% FCS to give a final concentration of $1 \times 10^6$ cells/ml, and 2 ml aliquots of the cell suspension were placed into sterile Falcon 2054 tubes.

Bacteria/PBMC Co-culture

Prepared bacterial preparations were thawed and vortexed vigorously. Bacteria were diluted in PBS and added as 20 µl aliquots to the PBMC cultures to give a final concentration of $1 \times 10^6$ cfu/ml or $1 \times 10^6$ inactivated cfu/ml for inactivated bacterial preparations. As positive controls for cytokine production, 1 µg/ml bacterial lipopolysaccharide (LPS) or 25 ng/ml phorbol 12-myristate 13-acetate (PMA) and 1 µg/ml Ionomycin were added to PBMC. As negative controls, tubes of PBMC received no additives. All tubes were incubated at 37° C. for 24 h, and the supernatants harvested by centrifugation. Supernatants were stored briefly at −20° C. before analysis of cytokine levels by ELISA.

Supernatants were assessed for levels of interferon-γ (Ifn-γ) and interleukin-10 (IL-10) by ELISA using matched capture and detection antibody pairs (R&D Systems Inc., Minneapolis, Minn.) according to the manufacturer's instructions. Where appropriate, supernatants were diluted in reagent diluent so that the level of the particular cytokine remained within the detection range of the standard curve of the ELISA.

Assessment of HN001 Inactivation

To measure the degree of inactivation by heat or UHP treatments, plate counts were performed on untreated and treated HN001 cells before dilution in PBS. As shown Table 7, UHP appeared to be slightly more efficient at killing than the heat treatment. Nonetheless, both methods resulted in a large kill rate, with the number of culturable cells assessed as being at least 5 logs lower than that of the starting cultures.

TABLE 7

Effect of heat treatment and UHP on HN001 viability

| Treatment | cfu/ml | log kill |
| --- | --- | --- |
| Untreated | $2 \times 10^{10}$ | — |
| Heat treated | $2 \times 10^5$ | 5.0 |
| 600 MPa | $6 \times 10^4$ | 5.5 |

Cytokine Responses of PBMC to Inactivated HN001

As markers of probiotic bioactivity, the production of IFN-γ and IL-10 by ex vivo PBMC as described above was examined. PBMC were isolated from peripheral blood samples obtained from a panel of healthy individuals (n=13), and aliquots of PBMC cultured with a 1:1 ratio of live bacteria or equivalent amounts of killed bacteria. After 24 h, culture supernatants were removed and analysed for levels of IFN-γ and IL-10 by ELISA. Results for each treatment across each individual were analysed by ANOVA and Bonferroni tests for multiple comparisons, with p<0.05 considered statistically significant.

Figure 14:
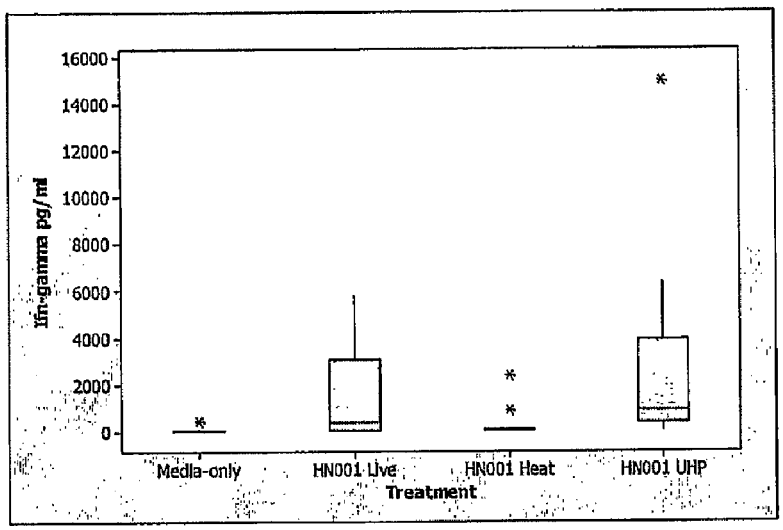
FIG. 14 is a box plot showing IFN-γ production by human ex vivo PBMC in response to *Lactobacillus rhamnosus* HN001 (HN001) treatments where each box represents one quartile above and below the median (horizontal line), the vertical line represents the total range, and asterisks denote outlier results and results are shown for PBMC cultured without HN001 (Media-only), with live HN001 (HN001 live), with heat inactivated HN001 (HN001 heat) or with UHP inactivated HN001 (HN001 UHP).

Studies by Cross et al. 2002 and others indicate IFN-γ may play a role in mediating the bioactivity of probiotic bacteria. As shown in FIG. 14, PBMC grown in media alone produced little detectable IFN-γ after 24. However, PBMC exposed to UHP-inactivated HN001 produced significantly more IFN-γ than PBMC in media only (p=0.006) or co-cultured with heat-inactivated HN001 (p=0.013), but similar IFN-γ levels as PBMC treated with live HN001 (p=0.91). Although there was a trend for increased IFN-γ production in response to live HN001 as compared to media-only and heat-inactivated HN001 treatments, the results were not statistically significant (p=0.23 and p=0.45, respectively).

Figure 15:
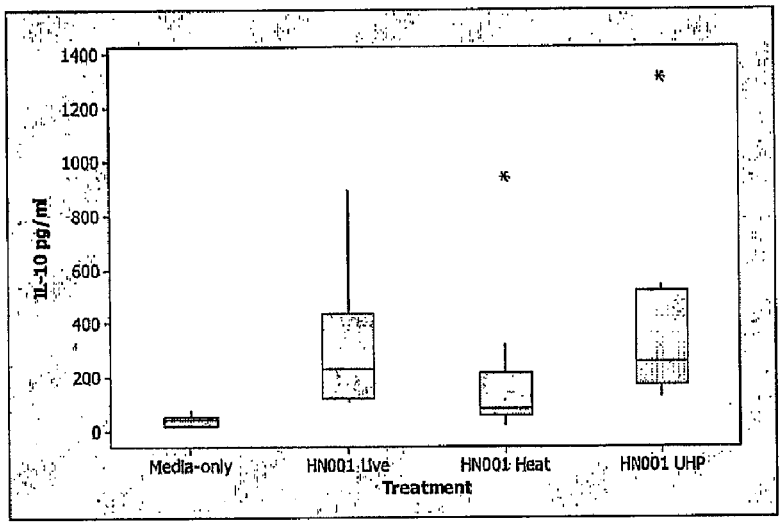
FIG. 15 is a box plot showing IL-10 production by human ex vivo PBMC in response to HN001 treatments.

IL-10 is generally considered to be an anti-inflammatory cytokine that inhibits TH1 T cell development and the production of a number of cytokines, including IFN-γ. Recently, IL-10 has become the focus of a number of clinical studies for its potential role in alleviating chronic inflammatory disease, including irritable bowel syndrome (IBS). As shown in FIG. 15, PBMC grown in media alone produced only small amounts of IL-10. PBMC co-cultured with HN001 led to significantly increased IL-10 production compared to PBMC in media alone (p=0.0001). While the use of heat-inactivated HN001 led to reduced IL-10 that bordered on statistical significance with respect to live HN001 (p=0.12), the use of UHP-inactivated HN001 led to IL-10 levels that were significantly higher than both media-only PBMC (p<0.0000) and PBMC cultured with heat-inactivated HN001 (p=0.003), but to similar levels as PBMC cultured with live HN001 (p=0.97). Accordingly, probiotic factors remain active after pressure treatment.

Mock-treated UHP HN001 (i.e. HN001 cells treated in the same way as UHP-treated HN001 except for exposure to increased pressure), showed no significant differences to live HN001 in terms of their ability to stimulate cytokine production by ex vivo PBMC.

Example 14

Effect of pH on Inactivation of HN001

Two cultures of HN001 were grown for 18 hours at 37° C. from 1 in 100 inoculums. One culture was washed once with sodium acetate, acetic acid buffer pH 5.0 (prepared according to Perrin & Dempsey, 1974) then resuspended in the same to a concentration of $1.6 \times 10^{11}$ cfu/ml. The other culture was treated identically except PBS pH 7.4 was substituted for sodium acetate, acetic acid buffer pH 5.0. Duplicate aliquots of each set of cells were placed in Beckman centrifuge tubes, sealed and pressure treated for 3 minutes, stored at 4° C. overnight then the degree of inactivation measured by plate counts (Table 8).

TABLE 8

Effect of pH on inactivation of *Lactobacillus rhamnosus* HN001.

| | cfu of HN001 | |
|---|---|---|
| Pressure (MPa) | Sodium acetate, acetic acid buffer - pH 5.0 | PBS buffer - pH 7.4 |
| No pressure treatment | 1.6E+11 | 1.6E+11 |
| 200 | 1.6E+11 | n.d. |
| 250 | 1.3E+11 | n.d. |
| 300 | 8.8E+10 | 1.1E+11 |
| 350 | 8.2E+09 | n.d. |
| 400 | 3.3E+09 | 2.3E+10 |
| 450 | 1.1E+07 | n.d. |
| 500 | 1.2E+05 | 2.8E+06 |
| 550 | <10 | n.d. |
| 600 | <10 | 170 |
| 700 | n.d. | 50 | n.d.—Not done.

Example 15

Effect of pH During HPP Treatment on HN001

HN001 bacterial cell cultures were resuspended in either PBS (pH 7.4) or acetate buffer (pH 5.0), inactivated by pressure treatment (600 MPa/3 minutes), and bioactivity compared to live and heat inactivated HN001 by measuring ability to stimulate IL-10 production by human ex vivo PBMC, as described above.

Figure 16:
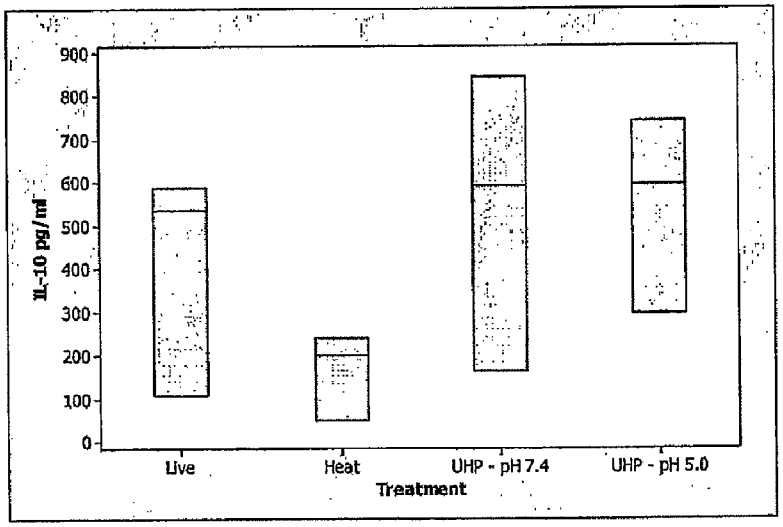
FIG. 16 is a box plot showing IL-10 production by human ex vivo PBMC in response to HN001 inactivated by UHP (600 MPa/3 minutes) in PBS buffer at pH 7.4 (UHP—pH 7.4) or in acetate buffer at pH 5.0 (UHP—pH 5.0) compared to live HN001 (Live) or heat-inactivated HN001 (Heat).

FIG. 16 shows the combined results from three individuals. IL-10 levels produced in response to HN001 inactivated by pressure treatment at either pH 7.4 or pH 5.0 were not significantly different to that observed for live HN001, but were significantly higher compared that for heat inactivated HN001 (p=0.043 and p=0.037, respectively).

Example 16

Enhanced Bioactivity Retention by Ligand Binding

Figure 17:
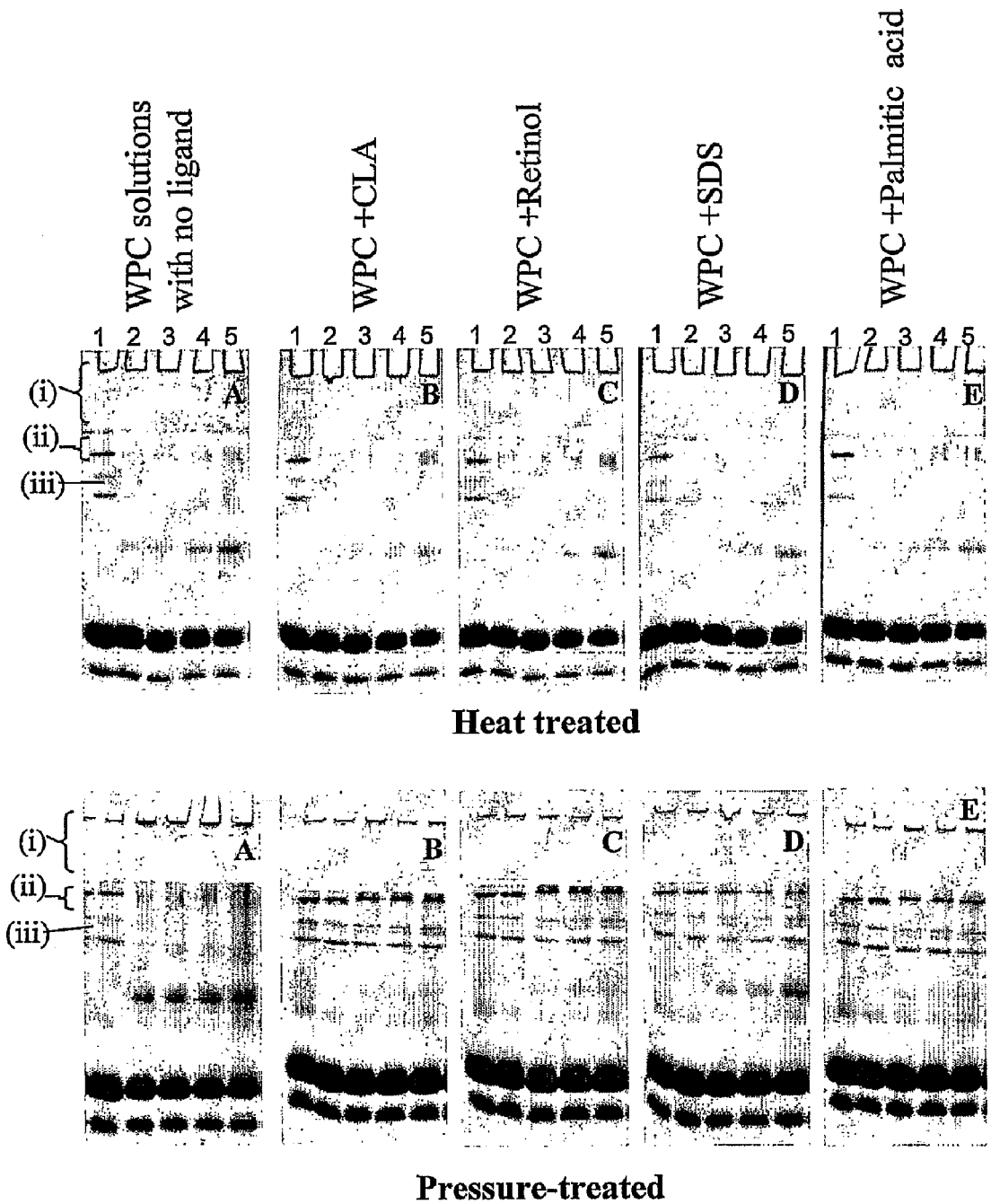
FIG. 17 is ten photographs of PAGE gels of heat-treated (90° C./1 to 4 minutes—upper row) or pressure-treated (600 MPa/1 to 4 minutes—lower row) 7% w/v WPC samples that were supplemented with hydrophobic ligands. In each gel, each Lane corresponds to a treatment time as follows: Lane 1: unprocessed control; Lane 2: 1 minute, Lane 3: 2 minutes; Lane 4: 3 minutes; and Lane 5: 4 minutes. High molecular weight aggregates are labeled "(i)", IgG "(ii)" and lactoferrin "(iii)".

2% solutions were prepared as whey protein concentrate (WPC) in water (Alacen 342, Fonterra Co-operative Group Ltd.) at pH 6.8. The following hydrophobic ligands were separately added to the WPC solutions (as 1:1 mole ratio to protein): conjugated linoleic acid, sodium dodecyl sulphate, retinol and palmitic acid. The solutions were then either pressure-treated at 600 MPa held for 1, 2, 3 or 4 minutes, or were heat-treated at 90° C. held for 1, 2, 3 or 4 minutes. The levels of IgG, lactoferrin and high molecular weight protein aggregates were evaluated on SDS-PAGE gels, and are compared to both an unprocessed control solution and a 2% WPC solution without the ligand added in FIG. 17.

The intensity of the bands is representative of the quantity of protein monomer which is present in the solution. In the unprocessed control samples (Lane 1), the area marked (i) is high molecular weight aggregates, the band marked (ii) is IgG and the band marked (iii) is lactoferrin. In the heat-treated samples (top), the intensity of the IgG and lactoferrin bands are substantially reduced, indicating the aggregation of protein and loss of monomeric protein. This is a result of protein denaturation and aggregation. This aggregation is seen in the heat treated samples irrespective of whether the hydrophobic ligand is present (B-E) or absent (A).

In contrast, the pressure-treated WPC solutions without the ligand showed reduced intensity (A, Lanes 2 to 5), whereas the pressure-treated WPC solutions with the various added hydrophobic ligands (B-E) showed substantially greater intensity.

The addition of the hydrophobic ligands to the bioactive-containing solution has enhanced the retention of bioactivity following a pressure treatment at near neutral pH.

Example 17

Solutions (6% w/v) of whey protein hydrolysates having ACE-I (Angiotensin-Converting Enzyme Inhibitory) activity were prepared and adjusted to pH 3.5, 4.5 or 7.0. Samples were pressure treated (600 MPa hold for 3 min or 600 MPa hold for 10 min) or heat treated (85° C. for 10 min or 90° C. for 10 min) and ACE-I activity and microbial content assessed compared to an untreated control. ACE-I activity was determined using FAPGG as a substrate (Product 305-10 ex Sigma Chemical Corporation, St Louis, MP, USA) according to the method of D. W. Cushman & H. S. Cheung (1971).

The results showed a greater than 3 log reduction in coliform count, yeasts and moulds, aerobic plate count, mesophilic spores and thermophile count for both pressure treated and heat treated samples compared to an untreated control. The ACE-I activities of the pressure and heat treated samples were within +/−2 standard deviations of the ACE-I activity of the unprocessed control and were not statistically different.

INDUSTRIAL APPLICATION

The methods of the present invention may be used to prevent the growth of unwanted microorganisms in compositions intended for use in the food and health industries, while avoiding or minimising effects on bioactive components that may be present.

Those persons skilled in the art will understand that the above description is provided by way of illustration only and that the invention is not limited thereto.

REFERENCES

Baker E, Baker H M, Kidd R D. Functional variations on a common structural framework Biochem. Cell Biol. (2002) 80, 27-34.

Bowie J U, Reidhaar-Olson J F, Lim W A, Sauer R T. Deciphering the message in protein sequences: tolerance to amino acid substitutions. Science. (1990) 247(4948):1306-10.

Copestake, D. E. J., Indyk, H., Otter, D. E. (2006). An affinity liquid chromatography method for the quantification of IgG in bovine colostrum products. J. AOAC Int. (In press).

Cross, M. L., Mortensen, R. R., et al. (2002). "Dietary intake of *Lactobacillus rhamnosus* HN001 enhances production of both Th1 and Th2 cytokines in antigen-primed mice". Medical Microbiology and Immunology (Berlin) 191: 49-53.

Cummings, J. H., Antoine, J-M., et al. (2004). "Gut Health and Immunity". European Journal of Nutrition 43: ii118-ii173.

Cushinal, D. W. and Cheung, H. S., Spectrophotometric assay and properties of the angiotensin-converting enzyme of rabbit lung. Biochem. Pharmacol. 20, 1637-1648, (1971).

Desmazeaud, M. (1993). Determination of indigenous antimicrobial proteins of milk, Bulletin of the International Dairy Federation (vol. 284). Lactoferrin (pp 29-42) (Chapter 3).

Domínguez, E., Pérez, M. D., Puyol, P., Sánchez, L., Calvo, M. (2001A). Effect of pH on antigen-binding activity of IgG from bovine colostrum upon heating. J. Dairy Res., 68, 511-518.

Elfstrand, L., Lindmark-Månsson, H., Paulsson, M., Nyberg, L., Åkesson, B. (2002). Immunoglobulins, growth factors and growth hormone in bovine colostrum and the effects of processing. Int. Dairy J., 12, 879-887.

Felipe X, Capellas M, Law A J R, Comparison of the effects of high-pressure treatment and heat pasteurization on the whey proteins in goat's milk, *Journal of Agricultural and Food Chemistry* 1997, 45, 627.

Huffman L M, Processing whey protein for use as a food ingredient, *Food Technology* 1996, 50(2), 49-52.

Huppertz T, Kelly A L, P. F. Fox, Effects of high pressure on constituents and properties of milk., *International Dairy Journal*, 2002, 12, 561-572.

Indyk H E, and Filonzi E L, Determination of Lactoferrin in Bovine Milk, Colostrum and Infant Formula by Optical Biosensor Analysis, *International Dairy Journal*, May 2005, 15(5): 429-438.

International Dairy Federation, "Whey. Proceedings of the Second International Whey Conference", 1998, Chicago, Ill., USA.

Kimmerlin T, Seebach D. 100 years of peptide synthesis: ligation methods for peptide and protein synthesis with applications to beta-peptide assemblies. J Pept Res. 2005 February; 65(2):229-60.

Korhonen H, Marnila P and Gill H S (2000). Bovine milk antibodies For Health. Br J Nutr 84(Suppl 1): S135-46.

Korhonen H, Pihlanto-Leppala A, Rantamaki P, Tupasela T, Impact of processing on bioactive proteins and peptides, *Trends in Food Science and Technology* 1998, 9, 307-319.

Leyer, G. J., Denin, V., et al. (2004). "Screening procedure for the selection of probiotics with immunomodulation potential". IFT Annual Meeting, Las Vegas, Nev.

Li.-Chan, E., Kummer, J. N., Losso, J. N., Kitts, D. D., Nakai, S. (1995). Stability of bovine immunoglobulins to thermal treatment and processing. Food Res. Int., 28, 9-16.

Li, S-Q., Zhang, H. Q., Balasubramanium, V. M., Lee, Y-Z., Bomser, J. A., Schwartz, S. J., Dunne, C. P. (2006). Comparison of effects of high-pressure processing and heat treatment on immunoactivity of bovine milk immunoglobulin G in enriched soymilk under equivalent microbial inactivation levels. 54, 739-746.

Li, S-Q., Zhang, Q. H., Lee, Y-Z. and Pham, T-V. (2003). Effects of pulsed electric fields and thermal processing on the stability of bovine immunoglobulin G (IgG) in enriched soy milk. J. Food Sci., 68, 1201-1207.

Lund, Barbara, M.; Baird-Parker, Tony C.; Gould, Grahame W. (Eds). Microbiological Safety and Quality of Food, Volumes 1-2, (2000) Springer-Verlag.

Manderson G A, Hardman M J & Creamer L K. Effect of heat treatment on the conformation and aggregation of beta-lactoglobulin A, B, and C. J. Agric. Food Chem. (1998) 46, 5052-5061.

Masuda T, Rehinarudo H Y, Suzuki K, Sakai T, Morichi T, The effect of high hydrostatic pressure treatment on the preservability and the immunological activity of bovine colostrum, *Asian-Australasian Journal of Animal Sciences* 2000 (13) 1323-1328.

McGinnis S., & Madden T. L., (2004) "BLAST: at the core of a powerful and diverse set of sequence analysis tools." Nucleic Acids Res. 32:W20-W25.

Mercenier, A., Hols, P., et al. (2004). "Screening and Construction of Probiotic Strains with Enhanced Protective Properties against Intestinal Disorders". Microbial Ecology in Health and Disease 16: 86-95.

Metz-Boutigue M H, Jolles J, Mazurier J, Schoentgen F, Legrand D, Spik G, Montreuil J, Jolles P. Human lactotransferrin: amino acid sequence and structural comparisons with other transferring. Eur J Biochem. 1984; 145(3): 659-76.

Nguyen L T, Schibli D J, Vogel J. Structural studies and model membrane interactions of two peptides derived from bovine lactoferricin. Journal of Peptide Science 2005, 11 (7) 379-89.

Palmano K P, and Elgar D E, Detection and quantification of lactoferrin in bovine whey samples by reverse-phase high-performance liquid chromatography on polystyrene-divinylbenzene, *Journal of Chromatography A*, 2002, 947, 307-311.

Paulsson, M. A., Svensson, U., Kishore, A. R., Naidu, A. S. (1993). Thermal behaviour of bovine lactoferrin in water and its relation to bacterial interaction and antibacterial activity. J. Dairy Sci., 76, 3711-3720.

Perrin, D D & Dempsey B. Buffers for pH and Metal Ion Control. (1974) Chapman and Hall. NY, USA.

Pierce A, Colavizza D, Benaissa M, Maes P, Tartar A, Montreuil J, Spik G. Molecular cloning and sequence analysis of bovine lactotransferrin. Eur J Biochem. 1991; 196(1): 177-84.

Sambrook, J; Fritsch E F; Maniatis T, (1989). Molecular Cloning: A Laboratory Manual. Cold Spring Harbour Lab Press, Cold Spring Harbour, New York.

Sienkiewicz T, and Riedel C (Eds) "Whey and whey utilisation" (Verlag, Germany, 1990).

Tatusova, T. A., Madden, T. L., "Blast 2 sequences—a new tool for comparing protein and nucleotide sequences", FEMS Microbiol Lett. (1999) 174:247-250.

Tetra Pak Processing Systems, Lund, Sweden, 1995.

Tonello C, Largeteau A, Jolibert F, Deschamps A, Demazeau G, Pressure effect on microorganisms and immunoglobulins of bovine colostrum, *High Pressure and Biotechnology*, Eds. C. Balny, R. Hayashi, K. Heremans, P. Masson. 1992 (224) 249-254.

Tsuji S, Hirata Y, Matsuoka K. Two apparent molecular forms of bovine lactoferrin. J Dairy Sci. 1989; 72(5):1130-6.

van der Kraan M I A, Groenink J, Nazmi K, Veerman E C I, Bolscher J G M, Nieuw Amerongen A V. Lactoferrampin: a novel antimicrobial peptide in the N1-domain of bovine lactoferrin. Peptides 2004, 25 (2) 177-83.

van Veen H A, Geerts M E, van Berkel P H, Nuijens J H. The role of N-linked glycosylation in the protection of human and bovine lactoferrin against tryptic proteolysis. Eur. J. Biochem. (2004) 271(4): 678-684.

Viejo-Diaz M, Andrés M T, Pérez-Gil J, Sanchez M, Fierro J F. Potassium Efflux Induced by a New Lactoferrin-Derived Peptide Mimicking the Effect of Native Human Lactoferrin on the Bacterial Cytoplasmic Membrane. Biochemistry (Moscow) 2003, 68 (2) 217-27.

Yoshida S, and Xiuyn, Ye. Isolation of Lactoperoxidase and Lactoferrins from Bovine Milk Acid Whey by Carboxymethyl Cation Exchange Chromatography. J Dairy Sci. 1991; 74:1439-1444.

Zadow J G (Ed) "Whey and Lactose Processing" (Elsevier Applied Science, London and New York, 1992).

What we claim is:

1. A method of treating a bioactive composition to maintain or increase its keeping quality comprising:
   (a) selecting a composition comprising at least one bioactive component selected from one or more proteins, one or more lipids, one or more protein hydrolysates, one or more lipid hydrolysates, one or more carbohydrates, or one or more probiotic factors, or a mixture thereof, the at least one bioactive component being able to retain a desired level of activity after a pressure treatment at a predetermined pressure of from about 350 to 1000 MPa, a pH of from about 3.0 to about 6.0; and a hold time of less than about 9 minutes; and
   (b) subjecting the composition to a pressure treatment at the predetermined pressure, pH, and hold time to prevent the growth of unwanted organisms that may be present in the composition while retaining at least a desired level of activity of the at least one bioactive component of at least about 35% of the activity of an untreated control.

2. A method of claim 1 wherein the bioactive component is selected from lactoferrin, lysozyme, one or more IgA, one or more IgD, one or more IgE, one or more IgG, one or more IgM, one or more growth factors, TGF $\beta$1, TGF $\beta$2, one or more probiotic factors, one or more non-polar lipids, one or more phospholipids, one or more sphingolipids, one or more gangliosides, one or more ceramides, or a mixture thereof.

3. A method of claim 1 wherein the bioactive component comprises one or more probiotic factors.

4. A method of claim 1 wherein the unwanted organism comprises a probiotic organism.

5. A method of claim 2 wherein the probiotic factor comprises one or more bacterial DNA motifs, one or more bacterial surface proteins, one or more bacterial small organic acids, one or more bacterial cell wall components, or a mixture thereof.

6. A method of claim 1 wherein the unwanted organism is one or more bacteria, one or more fungi, one or more molds, one or more yeasts, one or more algae, or a mixture thereof.

7. A method of claim 1 wherein the composition further comprises a hydrophobic ligand selected from palmitic acid, myristic acid, linoleic acid, conjugated linoleic acid, one or more phospholipids, one or more phosphatidylcholines, one or more sphingomyelins, one or more gangliosides, butyric acid, one or more omega-3 fatty acids, one or more phytosterols, one or more phytosterol esters, one or more phytosterol acetates, one or more omega-6 fatty acids, vitamin A, vitamin D, lycopene, or sodium dodecyl sulphate, or a mixture thereof and wherein the pH of the composition is from about 5.0 to 6.0.

8. A method of claim 1 wherein the composition is one of: a beverage, a yogurt, and a jelly.

9. A method of claim 1 wherein the component is one or more IgG, the treatment pressure is about 350 to 650 MPa, the pH is about 3.0 to 5.0, and hold time is about 0, 1, 2 or 3 minutes.

10. A method of claim 1 wherein the composition comprises a colostrum MPC, the component is IgG, the pressure is about 350 to 650 MPa, the pH is about 3.0 to 5.0, and the hold time is about 0, 1, 2 or 3 minutes.

11. A method of claim 1 wherein the composition comprises a colostrum MPI, the component is IgG, the pressure is about 350 to 650 MPa, the pH is about 3.0 to 5.0, and the hold time is about 0, 1, 2 or 3 minutes.

12. A method of claim 1 wherein the composition comprises a colostrum skim milk powder, the component is IgG, the pressure is about 350 to 650 MPa, the pH is about 3.0 to 5.0, and the hold time is about 0, 1, 2 or 3 minutes.

13. A method of claim 1 wherein the composition comprises a colostrum whey, the component is IgG, the pressure is about 350 to 650 MPa, the pH is about 3.0 to 5.0, and the hold time is about 0, 1, 2 or 3 minutes.

14. A method of claim 1 wherein the composition comprises a colostrum whey UF retentate, the component is IgG, the pressure is about 350 to 650 MPa, the pH is about 3.0 to 5.0, and the hold time is about 0, 1, 2 or 3 minutes.

15. A method of claim 1 wherein the composition comprises a hyperimmune milk, hyperimmune milk protein concentrate, hyperimmune whey protein concentrate, hyperimmune colostrum, hyperimmune colostrum milk protein concentrate or hyperimmune colostrum whey protein concentrate, the component is IgA, IgG, IgM or lactoferrin, the pressure is about 350 to 650 MPa, the pH is about 3.2 to 5.5, and the hold time is about 0, 1, 2 or 3 minutes.

16. A method of claim 1 wherein the component is lactoferrin, the pressure is about 350 to 650 MPa, the pH is about 3.0 to 6.0 and the hold time is about 0, 1, 2 or 3 minutes.

17. A method of claim 1 wherein the component is TGF-$\beta$1 or TGF-$\beta$2, the pressure is about 350 to 650 MPa, the pH is about 3.0 to 6.0 and the hold time is about 0, 1, 2 or 3 minutes.

18. A method of claim 1 wherein the composition is a yoghurt, the component is lactoferrin, the pressure is about 350 to 500 MPa, the pH is about 3.5 to 4.6 and the hold time is about 0, 1, 2 or 3 minutes.

19. A method of claim 1 wherein the composition is a beverage, the component is IgG, the pressure is about 350 to 650 MPa, the pH is about 3.0 to 5.0 and the hold time is about 0, 1, 2 or 3 minutes.

20. A method of claim 1 wherein the composition is a jelly, the component is lactoferrin, the pressure is about 350 to 650 MPa, the pH is about 3.0 to 5.0 and the hold time is about 0, 1, 2 or 3 minutes.

21. A method of claim 1 wherein the aerobic plate count of the composition after the pressure treatment is less than or equal to about 50,000 cfu/ml.

22. A composition treated according to the method of claim 1.

23. A method of claim 1, wherein the composition comprises at least one of the following: colostrum, a colostrum fraction, colostrum MPC, colostrum MPI, colostrum WPC, colostrum WPI, MPC, MPI, WPC, WPI, hyperimmune MPC, hyperimmune MPI, hyperimmune WPC, hyperimmune WPI and mixtures thereof.

24. A method of claim 8, wherein the beverage is an acidified beverage.

25. A method of claim 1 wherein the composition comprises colostrum, a colostrum fraction, colostrum MPC, colostrum MPI, colostrum WPC, colostrum WPI, hyperimmune MPC, hyperimmune MPI, hyperimmune WPC, or hyperimmune WPI, or a mixture thereof.

26. A method of claim 1 wherein the pH of the composition is about 3.0 to about 4.9.

27. A method of claim 1 wherein the pressure is held for about 0 to about 8 minutes.

28. A method of claim 1 wherein the pressure is held for about 0 to about 5 minutes.

29. A method of claim 1 wherein the pressure is held for about 0 to about 3 minutes.

30. A method of treating a probiotic composition comprising:
   (a) selecting a composition comprising one or more strains of probiotic microorganism having one or more probiotic factors, the probiotic factors being able to retain at least a desired level of activity after a pressure treatment at a predetermined pressure of from about 350 to 1000 MPa; and
   (b) subjecting the composition to a pressure treatment at the predetermined pressure to prevent the growth of the one or more strains of probiotic microorganism while retaining at least a desired level of activity of one or more probiotic factors of at least about 35% of the activity of an untreated control.

31. A method of claim 30 wherein the unwanted organism or the probiotic microorganism is selected from the group consisting of *Lactobacillus acidophilus, Lactobacillus delbrueckii* subsp. *bulgaricus, Lactobacillus casei, Lactobacillus crispatus, Lactobacillus johnsonii, Lactobacillus plantarum, Lactobacillus reuteri, Lactobacillus rhamnosus, Lactobacillus salivarius, Bifidiobacterium bifidum, Bifidiobacterium breve, Bifidobacterium infantis, Bifidiobacterium animalis* subsp. *lactis, Bifidobacterium longum,* or *Streptococcus thermophilus, Lactobacillus rhamnosus* HN001, *Bifidiobacterium animalis* subsp. *lactis* HN019, *Lactobacillus acidophilus* HN017, *Lactobacillus rhamnosus* HN067, *Lactobacillus johnsonii* NCC533 (La1), *Lactobacillus rhamnosus* GG, *Lactobacillus casei* Shirota, *Lactobacillus acidophilus* NCFM, *Lactobacillus plantarum* 299v, *Lactobacillus casei* DN114001, *Lactobacillus salivarius* UCC4331, *Bifidiobacterium animalis* subsp. *lactis* BB12, or *Bifidobacterium infantis* 35624, or a mixture thereof.

32. A method of claim 30 wherein the pressure is held for about 0 to about 8 minutes.

33. A method of claim 30 wherein the pressure is held for about 0 to about 5 minutes.

34. A method of claim 30 wherein the pressure is held for about 0 to about 3 minutes.

35. A method of treating a bioactive composition to maintain or increase its keeping quality comprising:
   (a) selecting a colostrum or hyperimmune milk composition comprising at least one bioactive component selected from one or more immunoglobulins, one or more lipids, one or more carbohydrates, or one or more probiotic factors, or a mixture thereof, the at least one bioactive component being able to retain a desired level of activity after a pressure treatment at a predetermined pressure of from about 350 to 1000 MPa, a pH of from about 3.0 to about 8.0; and a hold time of less than about 9 minutes; and
   (b) subjecting the composition to a pressure treatment at the predetermined pressure, pH and hold time to prevent the growth of unwanted organisms that may be present in the composition while retaining at least a desired level of activity of the at least one bioactive component of at least about 35% of the activity of an untreated control.

36. A method of claim 35 wherein the composition comprises colostrum MPC, colostrum MPI, colostrum WPC, colostrum WPI, hyperimmune MPC, hyperimmune MPI, hyperimmune WPC, or hyperimmune WPI, or a mixture thereof.

37. A method of claim 35 wherein the bioactive component is selected from one or more IgA, one or more IgD, one or more IgE, one or more IgG, one or more IgM, one or more non-polar lipids, one or more phospholipids, one or more sphingolipids, one or more gangliosides, one or more ceramides, or a mixture thereof.

38. A method of claim 35 wherein the pH of the composition is about 3.0 to about 4.9.

39. A method of claim 35 wherein the pressure is held for about 0 to about 8 minutes.

40. A method of claim 35 wherein the pressure is held for about 0 to about 5 minutes.

41. A method of claim 35 wherein the pressure is held for about 0 to about 3 minutes.

* * * * *

UNITED STATES PATENT AND TRADEMARK OFFICE
CERTIFICATE OF CORRECTION

PATENT NO.      : 8,062,687 B2
APPLICATION NO. : 11/908106
DATED           : November 22, 2011
INVENTOR(S)     : Timothy Joseph Carroll et al.

It is certified that error appears in the above-identified patent and that said Letters Patent is hereby corrected as shown below:

On Column 1, Line 61, change "20041032655" to --2004/032655--.

On Column 3, Line 50, change "Bifidiobacterium" to --Bifidobacterium--.

On Column 5, Line 33, change "W/W" to --w/w--.

On Column 5, Line 63, change "delbrueckil" to --delbrueckii--.

On Column 5, Line 67, change "Bifidiobacterium" to --Bifidobacterium--.

On Column 6, Line 1, change "Bifidiobacterium" to --Bifidobacterium--.

On Column 6, Line 7, change "Bifidiobacterium" to --Bifidobacterium--.

On Column 6, Line 17, change "Bifidiobacterium" to --Bifidobacterium--.

On Column 6, Line 21, change "rhanmosus" to --rhamnosus--.

On Column 6, Line 21, change "Bifidiobacterium" to --Bifidobacterium--.

On Column 10, Line 8-9, change "arabinoglactins," to --arabinogalactans,--.

On Column 13, Line 19-20, change "Bifidiobacterium" to --Bifidobacterium--.

On Column 13, Line 20, change "Bifidiobacterium" to --Bifidobacterium--.

On Column 13, Line 22, change "Bifidiobacterium" to --Bifidobacterium--.

On Column 13, Line 29, change "Bifidiobacterium" to --Bifidobacterium--.

On Column 14, Line 39, change "Bifidiobacterium" to --Bifidobacterium--.

On Column 14, Line 39-40, change "Bifidiobacterium" to --Bifidobacterium--.

On Column 14, Line 41, change "Bifidiobacterium" to --Bifidobacterium--.

On Column 14, Line 48, change "Bifidiobacterium" to --Bifidobacterium--.

On Column 16, Line 52, change "calorimetric" to --colorimetric--.

On Column 20, Line 26, after "cfu/ml" insert --.--.

On Column 24, Line 15, change "and or" to --and/or--.

On Column 25, Line 14, change "orglfiles" to --org/files--.

Signed and Sealed this
Eleventh Day of September, 2012

David J. Kappos
*Director of the United States Patent and Trademark Office*

CERTIFICATE OF CORRECTION (continued)
U.S. Pat. No. 8,062,687 B2

On Column 26, Line 27, change "µm)" to --nm)--.

On Column 26, Line 57, change "arabinoglactins," to --arabinogalactans,--.

On Column 31, Line 3, after "Hyperimmune" insert --(HI)--.

On Column 34, Line 1, change "(13)" to --(B)--.

On Column 35, Line 14, change "NM" to --MRS--.

On Column 39, Line 22, change "Cushinal," to --Cushman,--.

On Column 39, Line 24, after "(1971)" insert --.--.

On Column 40, Line 33, change "transferring." to --transferrins.--.

On Column 40, Line 43, after "307-311" insert --.--.

On Column 43, Line 37, in Claim 31, change "Bifidiobacterium" to --Bifidobacterium--.

On Column 43, Line 37-38, in Claim 31, change "Bifidiobacterium" to --Bifidobacterium--.

On Column 43, Line 38, in Claim 31, change "Bifidiobacterium" to --Bifidobacterium--.

On Column 43, Line 41, in Claim 31, change "Bifidiobacterium" to --Bifidobacterium--.

On Column 43-44, Line 46, in Claim 31, change "Bifidiobacterium" to --Bifidobacterium--.